(12) United States Patent
Livingston et al.

(10) Patent No.: US 12,391,721 B2
(45) Date of Patent: Aug. 19, 2025

(54) CRYSTAL FORMS OF BETA-NICOTINAMIDE MONONUCLEOTIDE

(71) Applicant: Metro International Biotech, LLC, Worcester, MA (US)

(72) Inventors: David J. Livingston, Worcester, MA (US); Andrew Carr, Hinxton (GB); Philippe Fernandes, Turnhout (BE)

(73) Assignee: Metro International Biotech, LLC, Worcester, MA (US)

( * ) Notice: Subject to any disclaimer, the term of this patent is extended or adjusted under 35 U.S.C. 154(b) by 0 days.

(21) Appl. No.: 19/025,101

(22) Filed: Jan. 16, 2025

(65) Prior Publication Data

US 2025/0171485 A1   May 29, 2025

Related U.S. Application Data

(63) Continuation of application No. 18/680,133, filed on May 31, 2024, now abandoned, which is a continuation of application No. 17/342,694, filed on Jun. 9, 2021, now abandoned, which is a continuation of application No. 16/454,457, filed on Jun. 27, 2019, now Pat. No. 11,059,847, which is a continuation of application No. 15/765,325, filed as application No. PCT/US2016/054776 on Sep. 30, 2016, now Pat. No. 10,392,415.

(60) Provisional application No. 62/236,657, filed on Oct. 2, 2015.

(51) Int. Cl.
    *C07H 19/048* (2006.01)
    *A61K 31/7052* (2006.01)

(52) U.S. Cl.
    CPC ........ *C07H 19/048* (2013.01); *A61K 31/7052* (2013.01); *C07B 2200/13* (2013.01)

(58) Field of Classification Search
    None
    See application file for complete search history.

(56) References Cited

U.S. PATENT DOCUMENTS

| | | |
|---|---|---|
| 3,201,389 A | 8/1965 | Fujimoto et al. |
| 3,451,997 A | 6/1969 | Fujimoto et al. |
| 4,411,995 A | 10/1983 | Whitesides et al. |
| 7,560,442 B2 | 7/2009 | Susilo |
| 7,776,326 B2 | 8/2010 | Milbrandt et al. |
| 7,977,049 B2 | 7/2011 | Sinclair et al. |
| 8,481,711 B2 | 7/2013 | Kaminishi et al. |
| 9,169,209 B2 | 10/2015 | Bair et al. |
| 9,295,688 B2 | 3/2016 | Milbrandt et al. |
| 9,458,172 B2 | 10/2016 | Bair et al. |
| 9,676,721 B2 | 6/2017 | Bair et al. |
| 9,822,129 B2 | 11/2017 | Bair et al. |
| 9,855,289 B2 | 1/2018 | Normington et al. |
| 9,861,651 B2 | 1/2018 | Brown et al. |
| 9,919,003 B2 | 3/2018 | Normington et al. |
| 9,975,915 B1 | 5/2018 | Migaud et al. |
| 10,000,519 B2 | 6/2018 | Migaud et al. |
| 10,214,552 B2 | 2/2019 | Fu et al. |
| 10,233,208 B1 | 3/2019 | Carr et al. |
| 10,392,415 B2 | 8/2019 | Livingston et al. |
| 10,392,416 B2 | 8/2019 | Livingston et al. |
| 10,548,913 B2 | 2/2020 | Normington et al. |
| 10,618,927 B1 | 4/2020 | Szczepankiewicz et al. |
| 11,059,847 B2 | 7/2021 | Livingston et al. |
| 11,180,521 B2 | 11/2021 | Kremsky et al. |
| 11,464,796 B2 | 10/2022 | Normington et al. |
| 11,787,830 B2 | 10/2023 | Kremsky et al. |
| 11,878,027 B2 | 1/2024 | Normington et al. |
| 11,939,348 B2 | 3/2024 | Szczepankiewicz et al. |
| 11,952,396 B1 | 4/2024 | Kremsky et al. |
| 2004/0224039 A1 | 11/2004 | Brucker |
| 2006/0002914 A1 | 1/2006 | Milbrandt et al. |
| 2007/0037809 A1 | 2/2007 | Nunes et al. |
| 2007/0149466 A1 | 6/2007 | Milburn et al. |
| 2008/0318892 A1 | 12/2008 | Pickering et al. |
| 2009/0143376 A1 | 6/2009 | Milburn et al. |
| 2010/0047177 A1* | 2/2010 | Milbrandt .............. A61P 25/00 424/9.2 |
| 2012/0107888 A1 | 5/2012 | Schmalisch et al. |
| 2012/0328526 A1 | 12/2012 | Kristian |
| 2013/0102771 A1 | 4/2013 | Kaminishi et al. |
| 2013/0273034 A1 | 10/2013 | Bair et al. |
| 2013/0295051 A1 | 11/2013 | Bair et al. |
| 2014/0221319 A1 | 8/2014 | Sinclair et al. |
| 2014/0275057 A1 | 9/2014 | Bair et al. |
| 2014/0294805 A1 | 10/2014 | Bair et al. |

(Continued)

FOREIGN PATENT DOCUMENTS

| | | |
|---|---|---|
| CN | 101497638 A | 8/2009 |
| CN | 101601679 B | 8/2011 |

(Continued)

OTHER PUBLICATIONS

"Nicotinamide Mononucleotide," Item No. 16411 Product Information, Cayman Chemical (2014).*

(Continued)

*Primary Examiner* — Patrick T Lewis
(74) *Attorney, Agent, or Firm* — Foley Hoag LLP; David P. Halstead; Tesia V. Chciuk

(57) ABSTRACT

The invention relates to crystalline forms of a β-nicotinamide mononucleotide, methods of their preparation, and related pharmaceutical preparations thereof. The invention also relates to preparations suitable for nutraceutical, veterinary, and agriculturally-relevant uses.

15 Claims, 8 Drawing Sheets

(56) References Cited

U.S. PATENT DOCUMENTS

| | | |
|---|---|---|
| 2015/0104384 A1 | 4/2015 | Bair et al. |
| 2015/0132280 A1 | 5/2015 | Lopez et al. |
| 2015/0175621 A1 | 6/2015 | Bair et al. |
| 2015/0258052 A1 | 9/2015 | Evans et al. |
| 2016/0002266 A1 | 1/2016 | Bair et al. |
| 2016/0022712 A1 | 1/2016 | Imai et al. |
| 2016/0038613 A1 | 2/2016 | Kaspar et al. |
| 2016/0168184 A1 | 6/2016 | Migaud et al. |
| 2016/0287621 A1 | 10/2016 | Sinclair et al. |
| 2016/0333041 A1 | 11/2016 | Fu et al. |
| 2016/0355514 A1 | 12/2016 | Bair et al. |
| 2016/0355539 A1 | 12/2016 | Migaud et al. |
| 2017/0066724 A1 | 3/2017 | Evans et al. |
| 2017/0182076 A1 | 6/2017 | Alvarez et al. |
| 2017/0189433 A1 | 7/2017 | Szczepankiewicz et al. |
| 2017/0204131 A1 | 7/2017 | Szczepankiewicz et al. |
| 2017/0210774 A1 | 7/2017 | Carlson et al. |
| 2017/0216262 A1 | 8/2017 | Bair et al. |
| 2017/0267709 A1 | 9/2017 | Migaud et al. |
| 2017/0304338 A1 | 10/2017 | Dellinger et al. |
| 2017/0368039 A1 | 12/2017 | Kenneth et al. |
| 2018/0030079 A1 | 2/2018 | Carlson et al. |
| 2018/0051253 A1 | 2/2018 | Chen |
| 2018/0086783 A1 | 3/2018 | Carlson et al. |
| 2018/0104248 A1 | 4/2018 | Lopez et al. |
| 2018/0134743 A1 | 5/2018 | Migaud et al. |
| 2018/0147227 A1 | 5/2018 | Normington et al. |
| 2018/0162895 A1 | 6/2018 | Fu et al. |
| 2018/0186824 A1 | 7/2018 | Migaud et al. |
| 2018/0228824 A1 | 8/2018 | Yoshino et al. |
| 2019/0328761 A1 | 10/2019 | Wu et al. |
| 2020/0031860 A1 | 1/2020 | Sauve |
| 2020/0157136 A1 | 5/2020 | Livingston et al. |
| 2020/0181188 A1 | 6/2020 | Rhonemus et al. |
| 2020/0352966 A1 | 11/2020 | Normington et al. |
| 2020/0368198 A1 | 11/2020 | Wu et al. |
| 2021/0030908 A1 | 2/2021 | Mason |
| 2022/0098229 A1 | 3/2022 | Livingston et al. |
| 2022/0144880 A1 | 5/2022 | Szczepankiewicz et al. |
| 2023/0149437 A1 | 5/2023 | Wu et al. |
| 2023/0158053 A1 | 5/2023 | Normington et al. |
| 2023/0210746 A1 | 7/2023 | Bermond et al. |
| 2023/0257412 A1 | 8/2023 | Kremsky et al. |
| 2024/0109932 A1 | 4/2024 | Kremsky et al. |
| 2024/0350523 A1 | 10/2024 | Normington et al. |

FOREIGN PATENT DOCUMENTS

| | | |
|---|---|---|
| CN | 102876759 A | 1/2013 |
| CN | 104367587 B | 6/2018 |
| JP | S41-12737 B2 | 7/1966 |
| JP | S41-15179 B2 | 8/1996 |
| JP | 2007-063167 A | 3/2007 |
| JP | 2008-501343 A | 1/2008 |
| WO | WO-2006/072809 A2 | 7/2006 |
| WO | WO-2006/094235 A1 | 9/2006 |
| WO | WO-2007/124447 A2 | 11/2007 |
| WO | WO-2010/135520 A1 | 11/2010 |
| WO | WO-2011/130595 A2 | 10/2011 |
| WO | WO-2012/004917 A1 | 1/2012 |
| WO | WO-2012/031196 A3 | 3/2012 |
| WO | WO-2012/031197 A1 | 3/2012 |
| WO | WO-2012/031199 A1 | 3/2012 |
| WO | WO-2012/094343 A1 | 7/2012 |
| WO | WO-2012/114204 A2 | 8/2012 |
| WO | WO-2012/150952 A1 | 11/2012 |
| WO | WO-2013/085555 A2 | 6/2013 |
| WO | WO-2013/127266 A1 | 9/2013 |
| WO | WO-2013/127267 A1 | 9/2013 |
| WO | WO-2013/127268 A1 | 9/2013 |
| WO | WO-2013/127269 A1 | 9/2013 |
| WO | WO-2013/130943 A1 | 9/2013 |
| WO | WO-2014/059034 A2 | 4/2014 |
| WO | WO-2014/074715 A1 | 5/2014 |
| WO | WO-2014/111906 A1 | 7/2014 |
| WO | WO-2014/146044 A1 | 9/2014 |
| WO | WO-2015/014722 A1 | 2/2015 |
| WO | WO-2015/069860 A1 | 5/2015 |
| WO | WO-2015/070280 A1 | 5/2015 |
| WO | WO-2015/073576 A1 | 5/2015 |
| WO | WO-2015/138969 A1 | 9/2015 |
| WO | WO-2015/186068 A1 | 12/2015 |
| WO | WO-2015/187649 A1 | 12/2015 |
| WO | WO-2016/014927 A2 | 1/2016 |
| WO | WO-2016/086088 A2 | 6/2016 |
| WO | WO-2016/086860 A1 | 6/2016 |
| WO | WO-2016/093515 A1 | 6/2016 |
| WO | WO-2016/144660 A1 | 9/2016 |
| WO | WO-2016/196941 A1 | 12/2016 |
| WO | WO-2016/210232 A1 | 12/2016 |
| WO | WO-2017/022768 A1 | 2/2017 |
| WO | WO-2017/059249 A1 | 4/2017 |
| WO | WO-2017/062311 A1 | 4/2017 |
| WO | WO-2017/079195 A1 | 5/2017 |
| WO | WO-2017/110317 A1 | 6/2017 |
| WO | WO-2017/114796 A1 | 7/2017 |
| WO | WO-2017/145151 A1 | 8/2017 |
| WO | WO-2017/161165 A1 | 9/2017 |
| WO | WO-2017/185549 A1 | 11/2017 |
| WO | WO-2017/218580 A1 | 12/2017 |
| WO | WO-2018/023205 A1 | 2/2018 |
| WO | WO-2018/023207 A1 | 2/2018 |
| WO | WO-2018/023208 A1 | 2/2018 |
| WO | WO-2018/023209 A1 | 2/2018 |
| WO | WO-2018/023210 A1 | 2/2018 |
| WO | WO-2018/047715 A1 | 3/2018 |
| WO | WO-2018/047716 A1 | 3/2018 |
| WO | WO-2018/052019 A1 | 3/2018 |
| WO | WO-2018/052020 A1 | 3/2018 |
| WO | WO-2018/089830 A1 | 5/2018 |
| WO | WO-2018/120069 A1 | 7/2018 |
| WO | WO-2018/132833 A1 | 7/2018 |
| WO | WO-2018/143258 A1 | 8/2018 |
| WO | WO-2019/152416 A1 | 8/2019 |
| WO | WO-2020/072497 A1 | 4/2020 |
| WO | WO-2020/197882 A1 | 10/2020 |
| WO | WO-2022/251491 A1 | 12/2022 |

OTHER PUBLICATIONS

"Non-antioxidant function of resveratrol", Vitamins 90:286-289 (2016).

ADP PubChem SID 134971804 deposited on Mar. 21, 2012.

Ahmadibeni et al., "Solid-Phase Synthesis of Symmetrical 5',5'-Dinucleoside Mono-, Di-, Tri-, and Tetraphosphodiesters," Organic Letters, 9(22): 4483-4486 (2007).

AMP PubChem SID 134970876 deposited on Mar. 21, 2012.

Anastasi et al., "New antiviral nucleoside prodrugs await application," Current medicinal chemistry, 10(18):1825-1843 (2003).

Arany et al., "HIF-independent regulation of VEGF and angiogenesis by the transcriptional coactivator PGC-1?," Nature, 451:1008-1012 (2008).

Arbiser et al., "Overexpression of VEGF 121 in Immortalized Endothelial Cells Causes Conversion to Slowly Growing Angiosarcoma and High Lebel Expression of the VEGF Receptors VEGFR-1 and VEGFR-2 in Vivo," Am J Pathol, 156(4):1469-1476 (2000).

Asher et al., "SIRT1 Regulates Circadian Clock Gene Expression through PER2 Deacetylation," Cell, 134:317 (2008).

Askew et al., "Skeletal muscle phenotype is associated with exercise tolerance in patients with peripheral arterial disease," J Vasc Surg, 41(5):802-807 (2005).

Atkinson et al., "Nicotinamide 6-Mercaptopurine Dinucleotide and Related Compounds: Potential Sources of 6-Mercaptopurine Nucleotide in Chemotherapy," Nature, 196: 35-36 (1962).

ATP PubChem SID 134972915 deposited on Mar. 21, 2012.

Baker et al., "Use of the mouse aortic ring assay to study angiogenesis," Nat Protoc, 7:89-104 (2012).

Baltgalvis et al., "Exercise performance and peripheral vascular insufficiency improve with AMPK activation in high-fat diet-fed mice," Am J Physiol Heart Circ Physiol, 306:H1128-H1145 (2014).

(56) References Cited

OTHER PUBLICATIONS

Barnea et al., "High-Fat Diet Delays and Fasting Advances the Circadian Expression of Adiponectin Signaling Components in Mouse Liver," Endicrinology 150:161 (2009).

Bassel-Duby et al., "Signaling Pathways in Skeletal Muscle Remodeling," Annu Rev Biochem, 75:19-37 (2006).

Bauer, "Polymorphism—A Critical Consideration in Pharmaceutical Development, Manufacturing, and Stability," Journal of Validation of Technology, 14(5):15-23 (2008).

Bazzanini et al., "Synthetic approaches to a mononucleotide prodrug of cytarabine," Nucleosides, Nucleotides, and Nucleic Acids, 24(10-12):1635-1649 (2005).

Belenky et al., "Nicotinamide riboside promotes Sir2 silencing and extends lifespan via Nrk and Urh1/Pnp1/Meu1 pathways to NAD+," Cell, 129(3):473-484 (2007).

Berghaeuser et al., "A Simple Preparation of an Enzyme Reactor Producing Nicotinamidemononucleotide," Biotechnology Letters, 3(7): 339-344 (1981).

Bieganowski et al., "Discoveries of nicotinamide riboside as a nutrient and conserved NRK genes establish a preiss-handler independent route to NAD+ in fungi and humans," Cell, 117:495-502 (2004).

Blanco et al., "VEGF and notch in tip and stalk cell selection," Cold Spring Harb Perspect Med, 3:a006569 (2013).

Bobeck et al., "Advances in nucleoside monophosphate prodrugs as anti-HCV agents," Antiviral Therapy—An Official Publication of the International Society for Antiviral Research, 15(7):935-950 (2010).

Bogan et al., "Nicotinic acid, nicotinamide, and nicotinamide roboside: A molecuar evaluation of NAD+ precursos vitamins in human nutrition," Annu Rev Nutr, 28:115-130 (2008).

Booth et al., "Molecular and cellular adaptation of muscle in response to exercise: perspectives of various models," Physiol Rev, 71:541-585 (1991).

Bordone et al., "Calorie restriction, SIRT1 and metabolism: understanding longevity," Nat Rev Mol Cell Biol, 6:298-305 (2005).

Borradaile et al., "NAD+, Sirtuins, and Cardiovascular Disease," Current Pharmaceutical Design, 15(1):110-117 (2016).

Borradaile et al., "Nicotinamide Phosphoribosyltransferase Imparts Human Endothelial Cells with Extended Replicative Lifespan and Enhanced Angiogenic Capacity in a High Glucose Environment," Aging Cells, 8:100-112 (2009).

Braidy et al., "Age related changes in NAD+ metabolism oxidative stress and sirt1 activity in wistar rats," PLoS One, 6:e19194 (2011).

Brittain et al., "X-Ray Diffraction of Pharmaceutical Materials," Profiles of Drug Substances, Excipients, and Related Methodology, 30:273-319 (2003).

Byrn et al., "Pharmaceutical solids: a strategic approach to regulatory considerations," Pharmaceut Res, 12(7):945-954 (1995).

Caira., Crystalline Polymorphism of Organic Compounds, Topics in Current Chemistry, 198: 163-208 (1998).

Canto et al., "The NAD+ Precursor Nicotinamide Riboside Enhances Oxidative Metabolism and Protects against High-Fat Diet-Induced Obesity," Cell Metab, 15:838-847 (2012).

Cardiac Medications, Heart.org, http://www.heart.org/en/health-topics/heart-attack/treatment-of-a-heart-attack/cardiac-medications (2015).

Cardus et al, "SIRT6 protects human endothelial cells from DNA damage, telomere dysfunction, and senescence," Cardiovasc Res, 97:571-579 (2013).

CAS Registry No. 108273-23-0 (1987).
CAS Registry No. 108489-22-1 (1987).
CAS Registry No. 1094-61-7 (1984).
CAS Registry No. 150035-58-8 (1993).
CAS Registry No. 321-02-8.
CAS Registry No. 906748-40-1 (2006).

Cattaneo-Pangrazzi et al., "The novel heterodinucleoside dimer 5-FdU-NOAC is a potent cytotoxic drug and a p53-independent inducer of apoptosis in the androgen-independent human prostate cancer cell lines PC-3 and DU-145", The Prostate 45(1): 8-18 (2000).

Cayman Chemical, "Beta-Nicotinamide mononucleotide," Item No. 16411 Product Information (2014).

Cayman Chemical, "Beta-Nicotinamide Mononucleotide," Item No. 16411 Safety Data Sheet, Cayman Chemical (2015).

Cebasek et al., "A novel staining method for quantification and 3D visualisation of capillaries and muscle fibres," Eur J Histochem, 48(2):151-158 (2004).

Chalkiadaki et al., "Muscle-specific SIRT1 Gain-of-Function Increases Slow-Twitch Fibers and Ameliorates Pathophysiology in a Mouse Model of Duchenne Muscular Dystrophy," PLoS Genet, 10(7):e1004490 (2014).

Chang et al., "Notch activation promotes endothelial survival through a PI3K-Slug axis," Microvasc Res, 89:80-85 (2013).

Chemical Cayman, "Nicotinic Acid Mononucleotide," Item No. 32883.

Cherney, "Osteoarthritis Medications List," Healthline, https://www.healthline.com/health/osteoarthritis/medications-list#nsaids (2016).

Chinsomboon et al., "The transcriptional coactivator PGC-1? mediates exercise-induced angiogenesis in skeletal muscle," Proc Natl Acad Sci, 106(50):21401-21406 (2009).

Cho et al., "Efficient synthesis of nucleoside aryloxy phosphoramidate prodrugs utilizing benzyloxycarbonyl protection," Tetrahedron, 67(30): 14 pages (2011).

Chung et al., "Regulation of SIRT1 in cellular functions: Role of polyphenols", Archives of Biochemistry and Biophysics 501(1):79-90 (May 5, 2010).

Congiatu et al., "Novel potential anticancer naphthyl phosphoramidates of BVdU: separation of diastereoisomers and assignment of the absolute configuration of the phosphorus center," Journal of medicinal chemistry, 49(2): 452-455 (2006).

Corda et al., "Functional aspects of protein mono-ADP-ribosylation," EMBO J, 22(9):1953-1958 (2003).

Costa et al., "The endothelial-erectile dysfunction connection: An essential update," J Sex Med, 6:2390-2404 (2009).

Cross et al., "Rules for the Nomenclature of Organic Chemistry. Section E: Sterohemistry," Pure Appl Chem, 45(1):11-30, (1976).

Das et al., "Nicotinamide mononucleotide, an NAD+ precursor, reverses age-associated decline in exercise capacity byincreasing skeletal muscle capillary density in a Sirt1-dependent manner.": 2015 Hobart Programme, Nov. 29, 2015-Dec. 2, 2015, Abstract published: Nov. 2015.

Database Registry Chemical Abstracts, Database Accession No. 807266-77-9, CAS Registry No. 807266-77-9 (Jan. 2, 2005).

De Souza, "Primer: Genome editing with engineered nucleases," Nat Meth, 9(1):27 (2012).

Dekker, Polymorphism in Pharmaceutical Solids, First Ed, pp. 184-208 (1999).

Dekker, Polymorphism in Pharmaceutical Solids, First Ed, pp. 7-8 (1999).

Diabetes Treatment, Drugs.com, https://www.drugs.com/diabetes-treatment.html (2018).

Dimmeler et al., "Endothelial cell apoptosis in angiogenesis and vessel regression," Res, 87:434-439 (2000).

Dowden et al., "Chemical Synthesis of the Novel CA 2+ Messenger NAADP," Nucleosides, Nucleotides and Nucleic Acids, 24(5-7):513-518 (2005).

Duscha et al., "Capillary Density of Skeletal Muscle," J Am Coll Cardiol, 33(7):1956-1963 (1999).

Eliseev et al., "Comparative study of antihypoxic properties of some nucleosides and nucleotides." Pharmaceutical Chemistry Journal 20.3 (1986): 160-162.

Erion et al., "Design, Synthesis, and Characterization of a Series of Cytochrome P450 3A-Activated Prodrugs (HepDirect Prodrugs) Useful for Targeting Phosph(on)ate-Based Drugs to the Liver," JACS Articles, 126: 5154-5163 (2004).

Escande et al., "Flavonoid apigenin is an inhibitor of the NAD+ ase CD38," Diabetes, 62:1084-1093 (2013).

Escudier et al., "Axitinib for the Management of Metastatic Renal Cell Carcinoma," Drugs R D, 11(2):113-126 (2011).

(56) References Cited

OTHER PUBLICATIONS

Extended European Search Report for EP Application No. 16833957.0 dated Dec. 21, 2018.
Extended European Search Report for EP Application No. 16852711.7 dated Feb. 11, 2019.
Extended European Search Report for EP Application No. 17883855.3 dated Dec. 15, 2020.
Extended European Search Report for EP Application No. 23197016.1 dated Oct. 18, 2023.
Fan et al., "Exercise Mimetics: Impact on Health and Performance", Cell Metabolism 25:242-247 (Feb. 7, 2017).
Fang et al., "Defective Mitophagy in XPA via PARP-1 Hyperactivation and NAD+/SIRT1 Reduction," Cell, 157(4):882-896 (2014).
Firestein et al., "The SIRT1 deacetylase suppresses intestinal tumorigenesis and colon cancer growth," PLoS One, 3(4):e2020 (2008).
Galli et al., "The Nicotinamide Phosphoribosyltransferase: A Molecular Link between Metabolism, Inflammation, and Cancer", Cancer Research, 70(1), pp. 8-11, 2010.
Garten et al., "Nampt: Linking NAD biology, metabolism, and cancer," Trends Endocrinol Metab, 20(3):130-138 (2009).
Gavande et al., "DNA repair targeted therapy: The past or future of cancer treatment?," Pharmacology & Therapeutics, 160:65-83 (2016).
Gockel et al., "Synthesis of an oligonucleotide with a nicotinamide mononucleotide residue and its molecular recognition in DNA helices," Organic & Biomolecular Chemistry, 13(41):10303-10309 (2015).
Gomes et al., "Declining NAD+ Induces a Pseudohypoxic State Disrupting Nuclear-Mitochondrial Communication druing Aging," Cell, 155(7):1624-1638 (2013).
Grieger et al., Adeno-associated virus as a gene therapy vector: Vector development, production and clinical application,s: Advances in Biochemical Engineering/Biotechnology, 99:119-145 (2005).
Guarani et al., "Acetylation-dependent regulation of endothelial notch signalling by the SIRT1 deacetylase," Nature 473(7346):234-238 (2011).
Guest et al., "Changes in Oxidative Damage, Inflammation and [NAD(H)] with Age in Cerebrospinal Fluid," PLOS One, 9(1):e85335 (2014).
Harasata et al., "Septal glucagon-like peptide I receptor expression determines suppression of cocaine-induced behavior," Neuropsychopharmacology, 40:1969-1978 (2015).
Hardie, "Minireview: the AMP-activated protein kinase cascade: the key sensor of cellular energy status", Endocrinology 144(12): 5179-5183 (2003).
Harrison et al., "Inhibition of Platelet Aggregation and the Platelet Release Reaction By alpha, omega Diadenosine polyphosphates," FEBS Letts 54(1):57-60 (1975).
Hart et al., "Resveratrol enhances exercise training responses in rats selectively bred for high running performace", Food and Chemical Toxicology 61:53-59 (2013).
Hirayama, Yuukikagoubutsu Kessyo sakusei Handbook—Genri to Know-how—(Handbook for Preparation of Crystals of Organic Compounds—Principle and Know-how—), Maruzen Co. Ltd., pp. 37-84 (2008).
Hood, "Plasticity in skeletal, cardiac, and smooth muscle," J Appl Physiol, 90:1137-1157 (1985).
Huang et al., "Metabolomics-driven identification of adenosine deaminase as therapeutic target in a mouse model of Parkinson's disease," Journal of Neurochemistry, 150: 282-295 (2019).
Imai et al., "NAD+ and sirtuins in aging and disease," Trends in Cell Biol, 24(8):464-471 (2014).
Imai et al., "Transcriptional silencing and longevity protein Sir2 is an NAD-dependent histone deacetylase," Nature, 403:795-800 (2000).
International Search Report and Written Opinion for International Application No. PCT/AU17/51435 dated Mar. 6, 2018.
International Search Report and Written Opinion for International Application No. PCT/US16/45855 dated Nov. 14, 2016.
International Search Report and Written Opinion for International Application No. PCT/US16/54776 dated Jan. 25, 2017.
International Search Report and Written Opinion for International Application No. PCT/US19/15672 dated May 15, 2019.
International Search Report and Written Opinion for International Application No. PCT/US20/23318 dated Jun. 24, 2020.
International Search Report and Written Opinion for International Application No. PCT/US22/31124 dated Oct. 6, 2022.
Invitation to Pay Additional Fees for International Application No. PCT/US22/31124 dated Aug. 5, 2022.
Kamel et al., "Pharmaceutical significance of cellulose: A review", Express Polym Letters 2(11): 758-778 (2008).
Kohsaka et al., "high-Fat Diet Disrupts Behavioral and Molecular Circadian Rhythms in Mice," Cell Metab, 6:414 (2007).
Kolluru et al., "Endothelial dysfunction and diabetes: Effects on angiogenesis, vascular remodeling, and wound healing," Int J Vasc Med, 918267, 1-30 (2012).
Koltai et al., "Exercise alters SIRT1, SIRT6, Nad and NAMPT levels in skeletal muscle of aged rats", Mechanisms of Ageing and Development 131(1):21-28 (Nov. 12, 2009).
Koni et al., "Conditional vascular cell adhesion molecule 1 deletion in mice: Impaired lymphocyte migration to bone marrow," J Exp Med, 193(6):741-753 (2001).
Korff et al., "Integration of endothelial cells in multicellular spheroids prevents apoptosis and induces differentiation," J Cell Biol, 143(5):1341-1352 (1998).
Kuznetsov et al., "Analysis of mitochondrial function in situ in permeabilized muscle fibers, tissues and cells," Nat Protoc, 3(6):965-976 (2008).
Lanza et al., "Primary Coronary Microvascular Dysfunction," Circulation, 121:2317-2325 (2010).
Le Couteur et al., "A Vascular Theory of Aging," Journal of Gerontology, 65A(10):1025-1027 (2010).
Lee et al., "A Chemical Synthesis of Nicotinamide Adenine Dinucleotide (NAD+)," Chemical Communications (Cambridge), 8: 729-730 (1999).
Lee, "A practical guide to pharmaceutical polymorph screening & selection," Asian Journal of Pharmaceutical Science 9(4):163-175 (2014).
Leisvuori et al. "5', 5'-Phosphodiesters and esterase labile triesters of 2'-C methylribonucleosides", ARKIVOC: Online Journal of Organic Chemistry (2012).
Limbourg et al., "Evaluation of postnatal arteriogenesis and angiogenesis in a mouse model of hind-limb ischemia," Nat Protoc, 4(12):1737-1746 (2009).
Lin et al., "Nicotinamide adenine dinucleotide, a metabolic regulator of transcription, longevity and disease," Curr Opin Cell Biol, 15:241-246 (2003).
Lin et al., "Transcriptional co-activator PGC-1? drives the formation of slow-twitch muscle fibres," Nature, 418:797-801 (2002).
Liu et al., "A Novel Preparation of Nicotinamide Mononucleotide," Nucleosides & Nucleotides, 13(5): 1215-1216 (1994).
Liu et al., "Enzymatic synthesis of polymers containing nicotinamide mononucleotide," Nucleic Acids Research, 23(18):3742 (1995).
Liu et al., "Synthesis of Phosphodiester-type Nicotinamide Adenine Dinucleotide Analogs," Tetrahedron, 65(40): 8378-8383 (2009).
Makarov et al., "Syntheses and chemical properties of B-nicotinamide riboside and its analogues and derivatives," Beilstein J Org Chem, 15: 401-430 (2019).
Massudi et al., "Age-associated changes in oxidative stress and NAD+ metabolism in human tissue," PloS One, 7(7): e42357 (2012).
McCormick, "The pathology vascular ("arteriovenous") malformations," J Neurosurg, 24:807-816 (1966).
McGuigan et al., "Certain phosphoramidate derivatives of dideoxy uridine (ddU) are active against HIV and successfully by-pass thymidine kinase," FEBS Letters, 351: 11-14 (1994).
McGuigan et al., "Phosphorodiamidates as a Promising New Phosphate Prodrug Motif for Antiviral Drug Discovery: Application to Anti-HCV Agents," Journal of Medicinal Chemistry, 54: 8632-8645 (2011).
Medications for Dermatitis, Drugs.com, https://www.drugs.com/condition/dermatitis.html (2018).
Medications for Obesity, Drugs.com, https://www.drugs.com/condition/obesity.html (2018).

(56) References Cited

OTHER PUBLICATIONS

Medications for Peripheral Neuropathy, Drugs.com, https://www.drugs.com/condition/peripheral-neuropathy.html (2018).
Medications for Thrombotic/Thromboembolic Disorder, Drugs.com, https://www.drugs.com/condition/thrombotic-thromboembolic-disorder.html (2018).
Menissier de Murcia et al., "Functional Interaction between PARP-1 and PARP-2 in chromosome stability and embryonic development in mouse," EMBO J, 22(9):2255-2263 (2003).
Mersmann et al., "Aspartoacylase-LacZ Knockin Mice: An Engineered Model of Canavan Disease," PLoS One, 6(5):e20336 (2011).
Migaud et al., "Probing Aplysia californica Adenosine 5'-Diphosphate Ribosyl Cyclase for Substrate Binding Requirements: Design of Potent Inhibitors," Biochemistry, 38:9105-9114 (1999).
Mikhailopulo et al., "Synthesis of glycosides of nicotinamide and nicotinamide mononucleotide," Synthesis, 5:388-389 (1981).
Mitchell et al., "The SIRT1 Activator SRT1720 Extends Lifespan and Improves Health of Mice Fed a Standard Diet," Cell Reports, 6: 836-843 (2014).
Moazed, "Enzymatic activities of Sir2 and chromatin silencing," Curr Opin Cell Biol, 13(2):232-238 (2001).
Montgomery et al., "Synthesis of Potential Anticancer Agents. XXVIII. Simple Esters of 6-Mercaptopurine Ribonucleotide2," The Journal of Organic Chemistry, 26(6):1929-1933 (1961).
Morscher et al., "Semi-quantitative multispectral optoacoustic tomography (MSOT) for volumetric PK imaging of gastric emptying," Photoacoustics, 2:103-110 (2014).
Mouchiroud et al., "NAD+ metabolism, a therapeutic target for age-related metabolic disease," Crit Rev Biochem Mol Biol, 48(4):397-408 (2013).
Mouchiroud et al., "The NAD+/Sirtuin Pathway Modulates Longevity through Activation of Mitochondrial URP and FOXO Signaling," Cell, 154:430-441 (2013).
Moynihan et al., "Increased dosage of mammalian Sir2 in pancreatic β cells enhances glucose-stimulated insulin secretion in mice," Cell Metab, 2:105-117 (2005).
Muzumdar et al., "A Global Double-Fluorescent Cre Reporter Mouse," Genesis, 45:593-605 (2007).
Nakahata et al., "The NAD+-Dependent Deacetylase SIRT1 Modulates CLOCK-Mediated Chromatin Remodeling and circadian Control," Cell, 134(2):329 (2008).
Nakai et al., Shin Seizaigaku (New Pharmacy), Nanzando Co. Ltd., 1st Edition, 2nd Printing, pp. 102-104, 217-236 (1984).
Nikiforov et al., "Pathways and Subcellular Compartmentation of NAD Biosynthesis in Human Cells," The Journal of Biological Chemistry, 286 (24):21767-21778 (2011).
Noseda et al., "Notch Activation Induces Endothelial Cell Cycle Arrest and Participates in Contact Inhibition: Role of P21Cip1 Repression," Mol Cell Biol, 24(20):8813-8822 (2004).
Novelle et al., "Resveratrol supplementation: Where are we now and where should we go?", Ageing Research Reviews 21:1-15 (2015).
Office Action for Chinese Application No. 201780086403.4 dated Apr. 6, 2022.
Office Action for Chinese Application No. 201780086403.4 dated Dec. 29, 2022.
Office Action for Japanese Application No. 2019-533084 dated Jun. 27, 2022.
Office Action for Japanese Application No. 2019-533084 dated Mar. 30, 2023.
Office Action for Japanese Application No. 2019-533084 dated Oct. 27, 2021.
Office Action for Korean Application No. 10-2019-7021500 dated Feb. 28, 2023.
Oomen et al., "Vascular endothelial growth factor A (VEGF-A) induces endothelial and cancer cell migration through direct binding to integrin ?9β1," J Biol Chem, 286(2):1083-1092 (2011).
Pearson et al., "Resveratrol delays age-related deterioration and mimics transcriptional aspects of dietary restriction with out extending lifespan," Cell Metab, 8(2):157-168 (2008).
Pencina et al., "MIB-626, an Oral Formulation of a Microcrystalline Unique Polymorph of Beta-Nicotinamide Mononucleotide, Increases Circulating Nicotinamide Adenine Dinucleotide and its Metabolome in Middle-Aged and Older Adults", J Gerontol A Biol Sci Med Sci, 2023, vol. 78, No. 1, 90-96.
Pencina et al., "Nicotinamide Adenine Dinucleotide Augmentation in Overweight or Obese Middle-Aged and Older Adults: A Physiologic Study", The Journal of Clinical Endocrinology & Metabolism, Feb. 6, 2023, 00, pp. 1-13.
Pertusati et al., "Medicinal chemistry of nucleoside phosphonate prodrugs for antiviral therapy," Antivir Chem Chemother, 22(5):181-203 (2012).
Petrelli et al., "NMN/NaMN Adenylyltransferase (NMNAT) and NAD Kinase (NADK) Inhibitors: Chemistry and Potential Therapeutic Applications," Current Medicinal Chemistry, 18: 1973-1992 (2011).
Pette et al., "Myosin isoforms, muscle fiber types, and transitions," Microsc Res Tech, 50:500-509 (2000).
Pfleiderer et al., "Zum Wirkungsmechanismus von Dehydrogenasen V. Uber die Bedeutung des Adenosindiphosphatrestes im Nicotinamid-Adenin-Dinucleotid," Biochimica et Biophysica Acta, 73:39-49 (1963).
Picard et al., "Sirt1 promotes fat mobilization in white adipocytes by repressing PPAR-y," Nature, 429:771-776 (2004).
Potente et al., "Emerging roles of SIRT1 in vascular endothelial homeostasis," Cell Cycle, 7:2117-2122 (2008).
Potente et al., "SIRT1 Controls Endothelial Angiogenic Functions During Vascular Growth," Genes & Development, 21: 2644-2658 (2007).
Preitner et al., "The Orphan Nuclear Receptor REV-ERBa Controls Circadian Transcription within the Positive Limb of the Mammalian circadian Oscillator," Cell, 110:251 (2002).
Price et al., "SIRT1 is required for AMPK activation and the beneficial effects of resveratrol on mitochondrial function," Cell Metab, 15:675-690 (2012).
Prior et al., "Sacropenia is associated with lower skeletal muscle capillarization and exercise capacity in older adults," J Gerontol A Biol Sci Med Sci, 71(8):1096-1101 (2016).
PubChem SID: 347731451 "Substance Record 321-02-8" retrieved online <https://pubchem.ncbi.nlm.nih.gov/substance/347731451>: 6 pages (Create Date Oct. 23, 2017).
Puech et al., "Nucleotidic prodrugs of anti-HIV dideoxynucleosides", Bioorganic & medicinal chemistry letters 2(6): 603-606 (1992).
Rajman et al., "Therapeutic Potential of NAD-Boosting Molecules: The In Vivo Evidence," Cell Metabolism, 27(3): 529-547 (2018).
Ramsey et al., "Cicadian clock feedback cycle through NAMPT-mediated NAD+ biosynthesis," Science, 324(5927):651-654 (2009).
Rechsteiner et al., "The Biosynthesis and Turnover of Nicotinamide Adenine Dinucleotide in Enucleated Culture Cells", The Journal of Cellular Physiology 84(3):409-421 (Dec. 1, 1974).
Redpath et al., "Nicotinamide Benzimidazolide Dinucleotides Non-Cyclisable Analogues of NAD+," Synlett, 25:2331-2336 (2014).
Repress et al., "Transthoracic echocardiography in mice," Journal of Visualized Experiments, 39:e1738 (2010).
Riemschneider et al., "Zur Beeinflussung von Stoffwechselvorgangen durch unphysiologische Verbindungen, IV: Nicotinylaminosaureester und Nucleosid-Deritvate," Insect repellent science, 41(3):99-106 (1976).
Rodgers et al., "Nutrient control of glucose homeostasis through a complex of PGC-1a and SIRT1," Nature, 434:113-118 (2005).
Rodionova et al., "Metabolic and bactericidal effects of targeted suppression of NadD and NadE enzymes in mycobacteria," mBio, 5(1):e00747-13 (2014).
Rose et al., "GYY4137, a Novel Water-Soluble, H2S-Releasing Molecule," Methods in Enzymology, 554:143-167 (2015).
Roskar et al., "Analytical Methods for Quantification of Drug Metabolites in Biological Samples," IntechOpen, Chapter 4:79-126 (2012).
Ross, "Visualization of mitochondrial respiratory function using cytochrome C oxidase / succinate dehydrogenase (COX/SDH) double-labeling histochemistry," J Vis Exp, 57:e3266 (2011).
Rowe et al., "Running Forward: New Frontiers in Endurance Exercise Biology," Circulation, 129(7):798-810 (2014).

(56) References Cited

OTHER PUBLICATIONS

Rudic et al., "BMAL1 and CLOCK, Two Essential Components of the Circadian Clock, Are Involved in Glucose Homeostasis," PLoS Biol, 2:e377 (2004).
Rutter et al., "Regulation of Clock and NPAS2 DNA Binding by the Redox State of NAD Cofactors," Science, 293(5529):510 (2001).
Sarma et al., "Investigations of Inter- and Intramolecular Interactions in Flavin-Adenine Dinucleotide by Proton Magnetic Resonance," Biochemistry, 7(12):4359-4367 (1968).
Sato et al., "A Functional Genomics Strategy Reveals Rora as a Component of the Mammalian Circadian Clock," Neuron, 43:527 (2004).
Sauve et al., "Sir2 regulation by nicotinamide results from switching between base exchange and deacetylation chemistry," Biochemistry, 42(31):9249-9256 (2003).
Schwartz et al., "The Effect of Growth Conditions on NAD+ and NADH Concentrations and the NAD+: NADH Ratio in Normal and Transformed Fibroblasts," J Biol Chem, 249(13): 4138-4143 (1974).
Sharma et al., "X-ray diffraction: a powerful method of characterizing nanomaterials," Recent Research in Science and Technology, 4:77-79 (2012).
Shioji, Kokei Seizai no Seizo Gijutsu (Manufacture Technology of Solid Tablet), CMC Publishing Co. Ltd., Popular Edition, 1st Printing, pp. 9-14 (2003).
Sleep Disorders: Medications for Circadian Rhythm Disorders, WebMD, https://www.webmd.com/sleep-disorders/circadian-rhythm-disorder-medications#1 (2018).
Smith et al., "A combinatorial approach to create artificial homing endonucleases cleaving chosen sequences," Nucleic Acids Research, 34(22):e149 (2006).
Smith et al., "A phylogenetically conserved NAD+-dependent protein decetylase activity in the Sir2 protein family," Proc Natl Acad Sci, 97(12):6658-6663 (2000).
Soto-Gamez et al., "Therapeytic interventions for aging: the case of cellular senescence," Drug Discovery Today, 22(5):786-795 (2017).
Stein et al., "Expression of nampt in hippocampal and cortical excitatory neurons is critical for cognitive function," J Neurosci, 34(17): 5800-5815 (2014).
Stein et al., "Scientific ablation on Nampt in adult neural stem cells recapitulates their functional defects during aging," EMBO J, 33(12):1321-1340 (2014).
Stieger et al., "7:Recrystallization of Active Pharmaceutical Ingredients," Crystallization—Science and Technology, 183-204 (2012).
Takada, "API form screening and selection in drug discovery stage", Pharm Stage, 6(10):20-25. (2007).
Takahashi et al., "The Genetics of Mammalian Circadian Order and Disorder: Implications for Physiology and Disease," Nat Rev Genet, 9(10):764 (2008).
Tan et al., "Precision Editing of Large Animal Genomes," Adv Genet, 80: 37-97 (2012).
The Chemical Society of Japan Ed., 4th Edition Jikken Kagaku Kouza 1 Kihon Sousa I (4th Edition Experimental Chemistry 1 Basic Operation I), Maruzen Co. Ltd., 2nd Printing, pp. 184-186 (1996).
Thorpe et al., "Lipoamide Dehydrogenase from Pig Heart. Pyridine Nucleotide Induced Changes in Monoalkylated Two-Electron Reduced Enzyme," Biochemistry, 20: 1507-1513 (1981).
Turek et al., "Obesity and Metabolic Syndrome in Circadian Clock Mutant Mice," Science, 308:1043 (2005).
Turner et al., "Enhancement of muscle mitochondrial oxidative capacity and alterations in insulin action are lipid species dependent," Diabetes, 58:2547-2554 (2009).
Uddin et al., "Head to Head Comparison of Short-Term Treatment with the NAD+ Precursos Nicotinamide Mononucleotide (NMN) and 6 Weeks of Exercise in Obese Female Mice," Front Pharmacol, 7(258):1-11 (2016).
United States Department of Health and Human Services. "Guidance for Industry Pyrogen and Endotoxin Testing: Questions and Answers," pp. 1-10 (2012).
United States Pharmacopeia General Chapter <151> Pyrogen Test, 2 pages.
Urnov et al., "Genome editing with engineered zinc finger nucleases," Nat Rev Genet, 11(9):636-646 (2010).
Van Beijnum et al., "Isolation of endothelial cells from fresh tissues," Nat Protoc, 3:1085-1091 (2008).
Vasko et al., "Endothelial sirtuin 1 deficiency perpetrates nephrosclerosis through downregulation of matrix metalloproteinase-14: Relevance to fibrosis of vascular senescence," J Am Soc Nephrol, 25:276-291 (2014).
Verdin et al., "NAD+ in aging, metabolism, and neurodegeneration", Science 350(6265):1208-1213 (Dec. 4, 2015).
Vinciguerra et al., "SirT1 in muscle physiology and disease: lessons from mouse models", Disease Models & Mechanisms 3:298-303 (2010).
Walt et al., "An Efficient Chemical and Enzymatic Synthesis of Nicotinamide Adenine Dinucleotide (NAD+)," Journal of the American Chemical Society, 106(1): 234-239 (1984).
Wang et al., "A local mechanism mediates NAD-dependent protection of axon degeneration," J Cell Biol, 170(3):349-355 (2005).
Wang et al., "Intracellular NAMPT-NAD+-SIRT1 Cascade Improves Post-Ischaemic Vascular Repair by Modulating Notch Signalling in Endothelial Progenitors," Cardiovascular Research, 104: 477-488 (2014).
Wang et al., "P7C3 neuroprotective chemicals function by activating the rate-limiting enzyme in NAD salvage," Cell, 158(6):1324-1334 (2014).
Wei et al., "Aortopathy in a mouse model of marfan syndrome is not mediated by altered transforming growth factor β signaling," J Am Heart Assoc, 1-14 (2017).
Wen et al., "Ca2+/calmodulin-dependent protein kinase kinase β phosphorylation of Sirtuin 1 in endothelium is atheroprotective," Proc Natl Acad Sci, 110:e2420-e2427 (2013).
Wiemer et al., "Prodrugs of Phosphnates and Phosphates: Crossing the Membrane Barrier," Topics in Current Chemistry, 360:115-160 (2014).
Woenckhaus, "Synthesen und biochemische Eigenschaften wassertoffubertragender Coenzye modelle," Chemische Berichte, 97(9):2439-2446 (1964).
Wound Care Medications, GoodRx.com, https://www.goodrx.com/wound-care/drugs (2018).
Yamada et al., "The simultaneous measurement of nicotinamide adenine dinucleotide and related compounds by liquid chromatography/electrospray ionization tandem mass spectrometry," Analytical Biochemistry, 352:282-285 (2006).
Yang et al., "NAD+-dependent Deacetylase SIRT3 Regulates Mitochondrial Protein Synthesis by Deacetylation of the Ribosomal Protein MRPL10," J Biol Chem, 285: 7417-7429 (2010).
Yoshino et al., "Nicotinamide Mononucleotide, a Key NAD+ Intermediate, Treats the Pathology of Diet- and Age-Induced Diabetes in Mice," Cell Metab, 14(4): 528-536 (2011).
Zhang et al., "Hydrogen Sulfide, the Next Potent Preventive and Therapeutic Agent in Aging and Age-Associated Diseases," Molecular and Cellular Biology, 33(6): 1104-1113 (2013).
Zhang et al., "Liung endothelial HO-1 targeting in vivo using lentiviral miRNA regulates apoptosis and autophagy during oxidant injury," FASEB J, 27:4014-4058 (2013).
Zhao et al., "SIRT1 and exercises", Chinese Journal of Gerontology, vol. 31, No. 5, published on May 4, 2011, pp. 906-910.
Zhu et al., "A hydrazine coupled cycling assay validates the decrease in redox ratio under starvation in *drosophilia*," PLoS One, 7(10):e47584 (2012).
Bauer, "Pharmaceutical solids-the amorphous phase." Journal of Validation Technology 15.3 (2009): 63.
Extended European Search Report for EP Application No. 22812156.2 dated Apr. 14, 2025.

* cited by examiner

CRYSTAL FORMS OF BETA-NICOTINAMIDE MONONUCLEOTIDE

CROSS-REFERENCE TO RELATED APPLICATION

This Application is a continuation of U.S. application Ser. No. 18/680,133, filed May 31, 2024, which is a continuation of U.S. application Ser. No. 17/342,694, filed Jun. 9, 2021, which is a continuation of U.S. application Ser. No. 16/454,457, filed Jun. 27, 2019, which is continuation of U.S. application Ser. No. 15/765,325, filed Apr. 2, 2018, which is a U.S. National Stage entry under 35 U.S.C. § 371 of International Application PCT/US16/54776, filed Sep. 30, 2016, which claims the benefit of priority to U.S. Provisional Patent Application No. 62/236,657, filed Oct. 2, 2015. The contents of each of these applications is incorporated by reference herein in its entirety.

BACKGROUND

β-Nicotinamide mononucleotide (NMN) has recently garned attention for its use in the treatment, amelioration, mitigation, slowing, arrest, prevention and/or reversal of age-associated degenerative changes, such as age-related obesity, age-related increases in blood lipid levels, age-related decreases in insulin sensitivity, age-related decreases in memory function, and age-related changes in eye function such as macular degeneration.

Given the therapeutic benefits associated with this compound, there is a need for improved compositions of NMN. Further, there is a need for improved methods for preparing and formulating β-nicotinamide mononucleotide.

SUMMARY OF INVENTION

One aspect of the invention relates to a crystalline compound having the structure of formula (I),

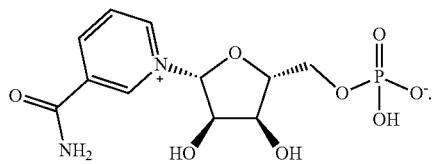

(I)

Another aspect of the invention relates to methods for preparing the crystalline compounds of formula (I).

In certain embodiments, the present invention provides a pharmaceutical preparation suitable for use in a human patient, comprising a crystalline compound of formula (I), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient.

DETAILED DESCRIPTION OF THE DRAWINGS

Figure 7:
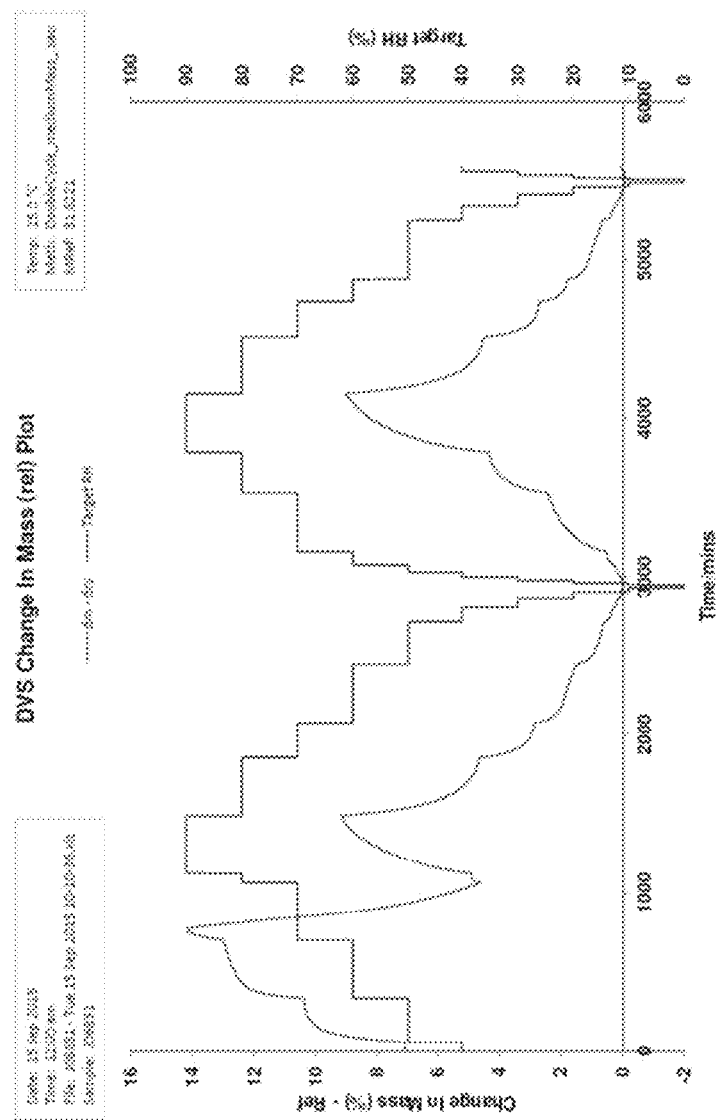

FIG. 7 shows a dynamic vapor sorption change in mass plot for amorphous NMN. When a sample of amorphous NMN is exposed to atmospheric humidity, the sample goes through phases. FIG. 7 shows the mass change over time. The amorphous sample is hygroscopic until it deliquesces and starts crystallizing. The weight loss below 1000 min shows a crystallisation event. Once crystallised, the material remains crystalline, retaining the same XRPD pattern after a double cycle, but still shows the ability to pick up mass reversibly (up to 9% w/w change).

Figure 8:
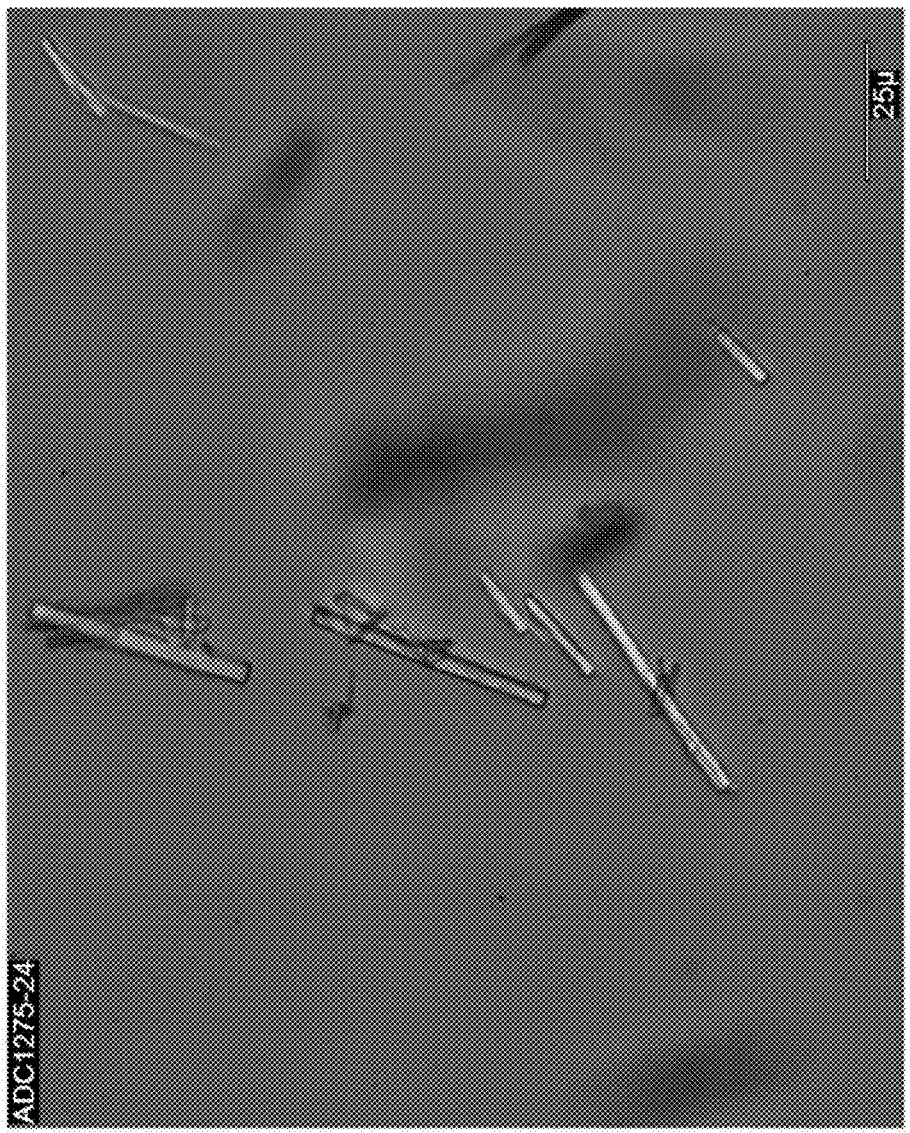

FIG. 8 is an image showing single crystals of NMN Form 1, observed under a polarized microscope.

DETAILED DESCRIPTION OF THE INVENTION

In certain embodiments, the invention provides a crystalline compound having the structure of formula (I),

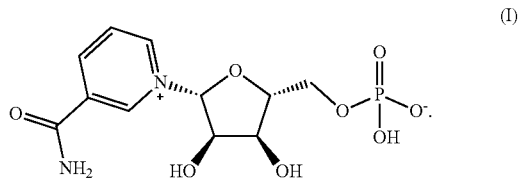

(I)

In certain embodiments, a crystalline compound of formula (I) is not solvated (e.g., the crystal lattice does not comprise molecules of a solvent). In certain embodiments, the crystalline compound of formula (I) is anhydrous, or substantially anhydrous. In certain alternative embodiments, a crystalline compound of formula (I) is solvated. In certain such embodiments, the crystalline compound of formula (I) is a dimethylsulfoxide (DMSO) solvate.

Any crystalline compound described herein may be used in the manufacture of a medicament for the treatment of any diseases or conditions disclosed herein.

In certain embodiments, the compounds of the present invention can assemble into more than one crystal formation. In an exemplary embodiment, the crystalline compound having the structure of formula (I) exists as "form I" and "form II", as described in detail below. These different forms are understood as "polymorphs" herein.

In certain embodiments, the polymorph of the crystalline compound is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, an anhydrous crystalline compound of formula (I) has 2θ values 20.03; 20.14; 21.83; and 25.73. In further embodiments, the anhydrous crystalline compound has 2θ values 20.03; 20.14; 21.03; 21.83; 23.08; 23.39; 25.73; and 26.59. In yet further embodiments, the anhydrous crystalline compound has 2θ values 7.70; 11.54; 12.64; 16.03; 18.99; 20.03; 20.14; 20.83; 21.03; 21.83; 23.08; 23.39; 25.48; 25.73; 26.59; and 29.78. In still yet further embodiments, the anhydrous crystalline compound has 2θ values 7.70; 9.95; 11.54; 12.64; 16.03; 18.18; 18.99; 19.16; 19.44; 20.03; 20.14; 20.83; 21.03; 21.83; 22.44; 23.08; 23.39; 23.89; 24.08; 24.53; 24.68; 25.05; 25.48; 25.73; 26.08; 26.59; 27.33; 27.67; 29.78; and 29.92.

Figure 1:
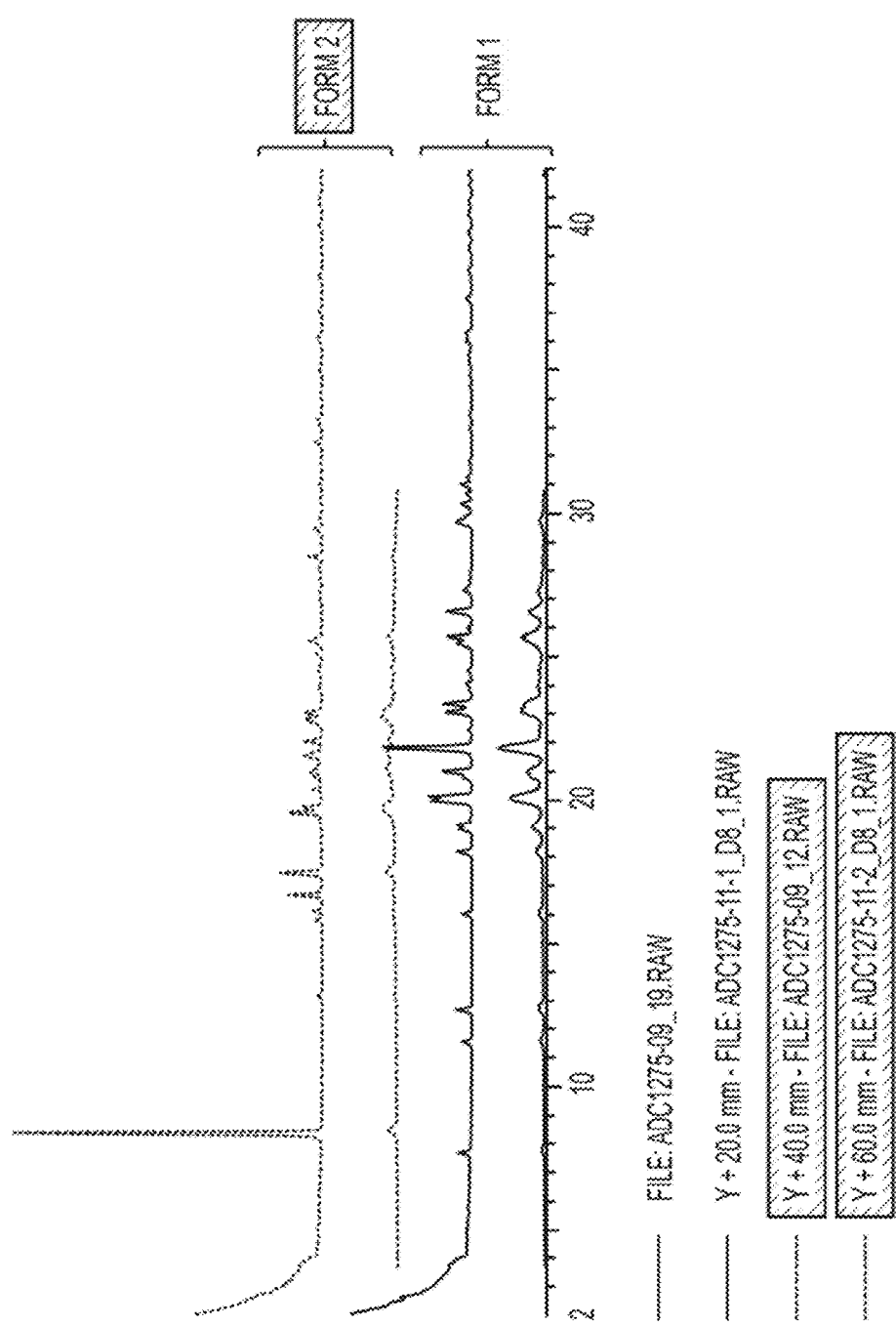
FIG. 1 shows the XRPD patterns of β-nicotinamide mononucleotide (NMN) forms 1 and 2.
Figure 2:
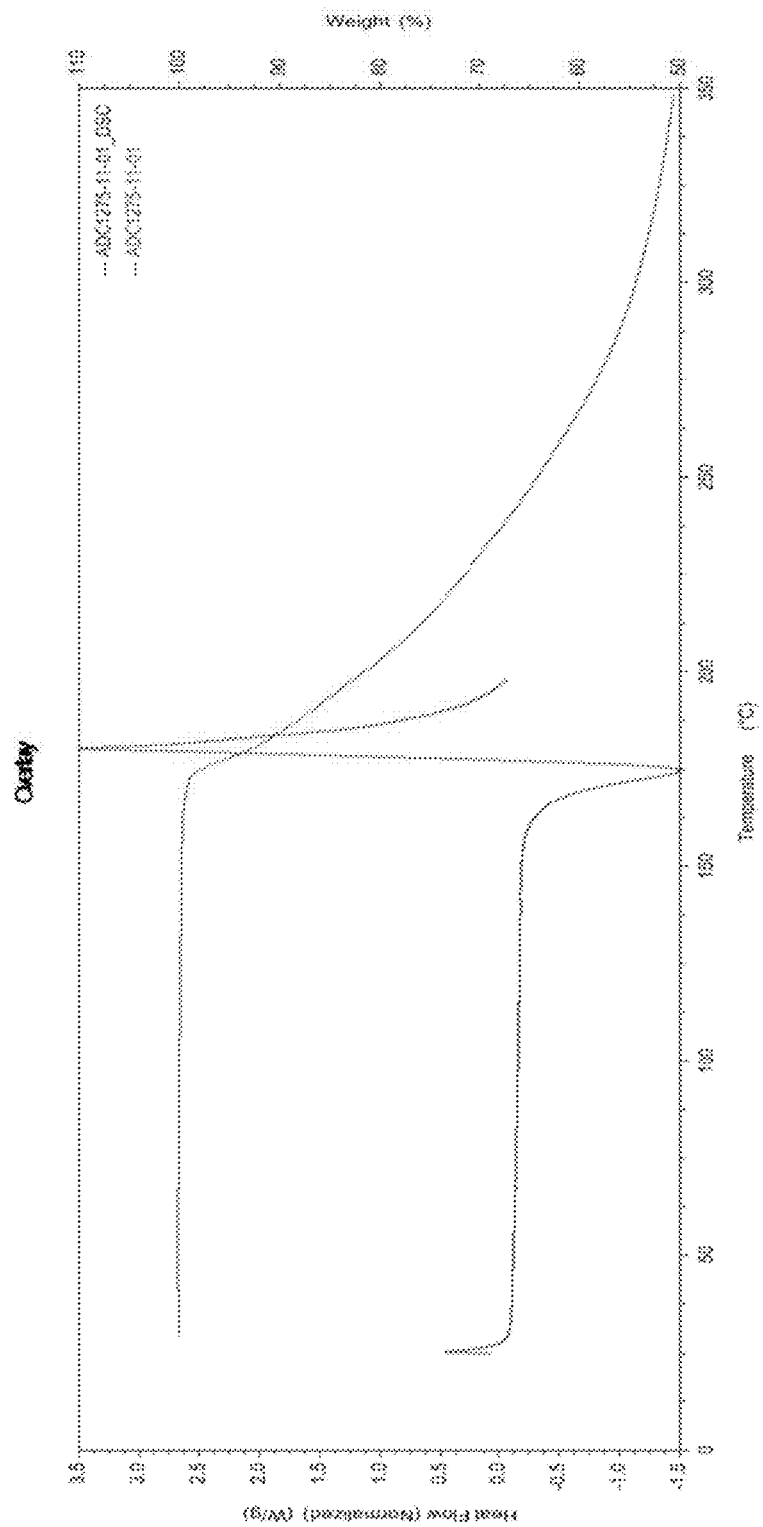
FIG. 2 shows the differential scanning calorimetry thermogram of Form 1.
Figure 3:
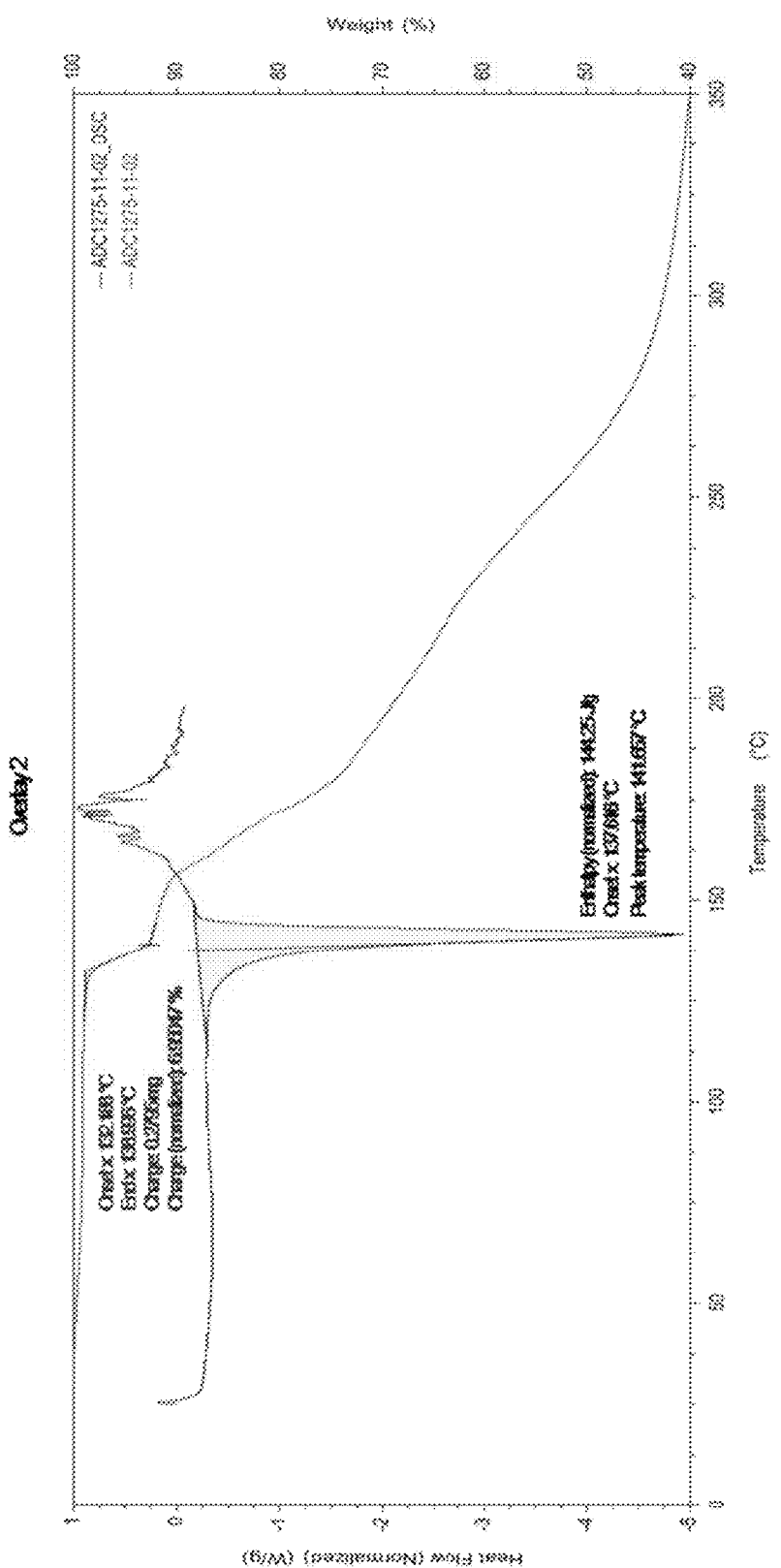
FIG. 3 shows the differential scanning calorimetry thermogram of Form 2.
Figure 4:
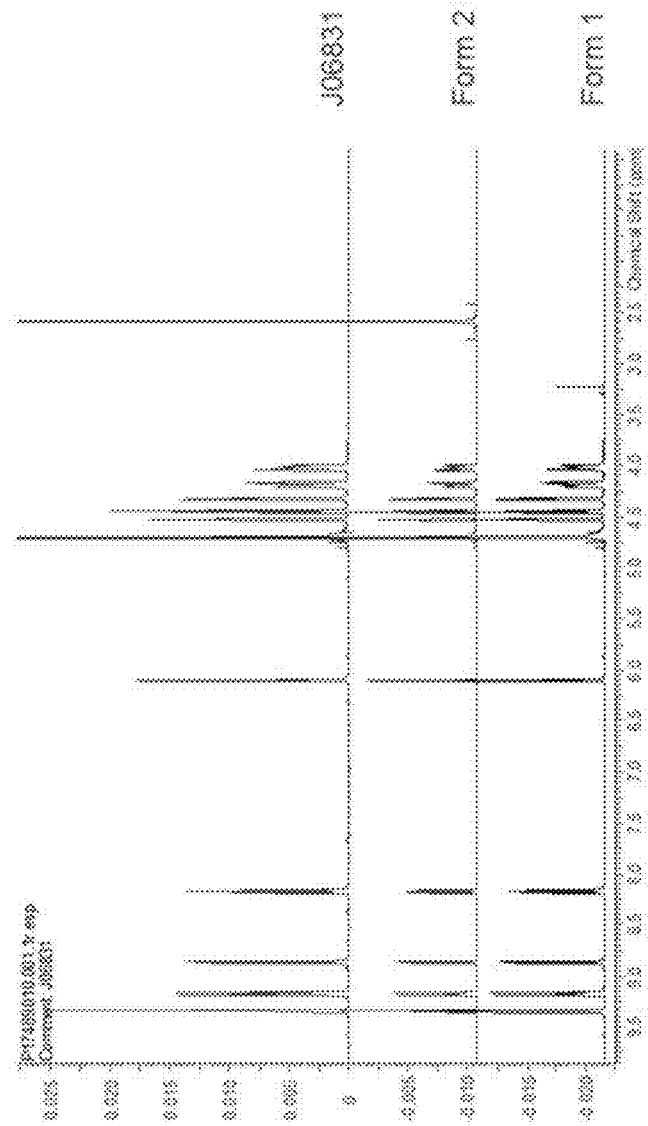
FIG. 4 shows $^1$H NMR spectra of the amorphous NMN, NMN Form 1, and NMN Form 2 after drying under vacuum. As shown in the spectra, Form 1 is substantially anhydrous, and Form 2 has about 1.1-1.2 DMSO molecules per molecule NMN.
Figure 5:
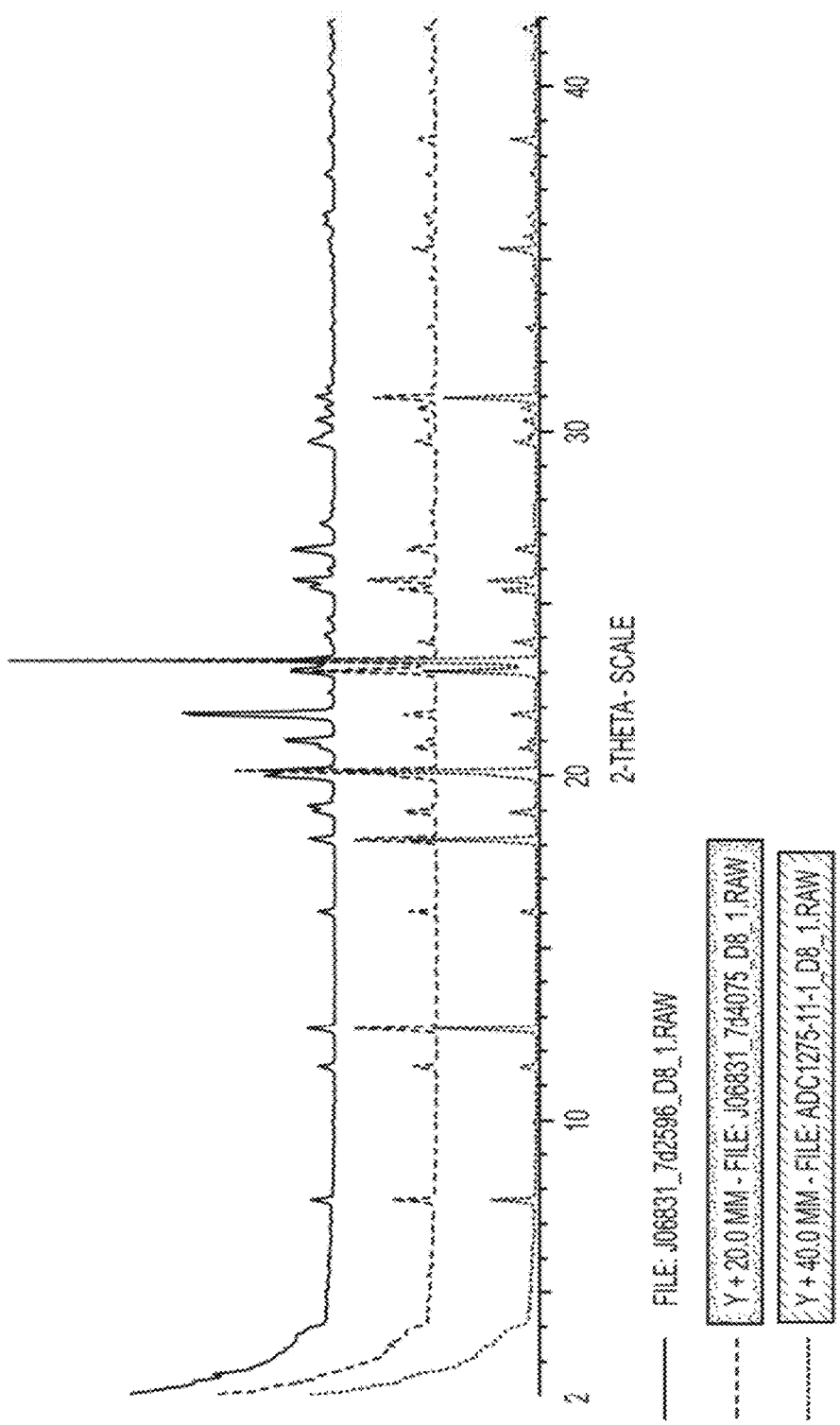
FIG. 5 shows a comparison of XRPD patterns of amorphous NMN, amorphous NMN post-storage, and NMN Form 1.
Figure 6:
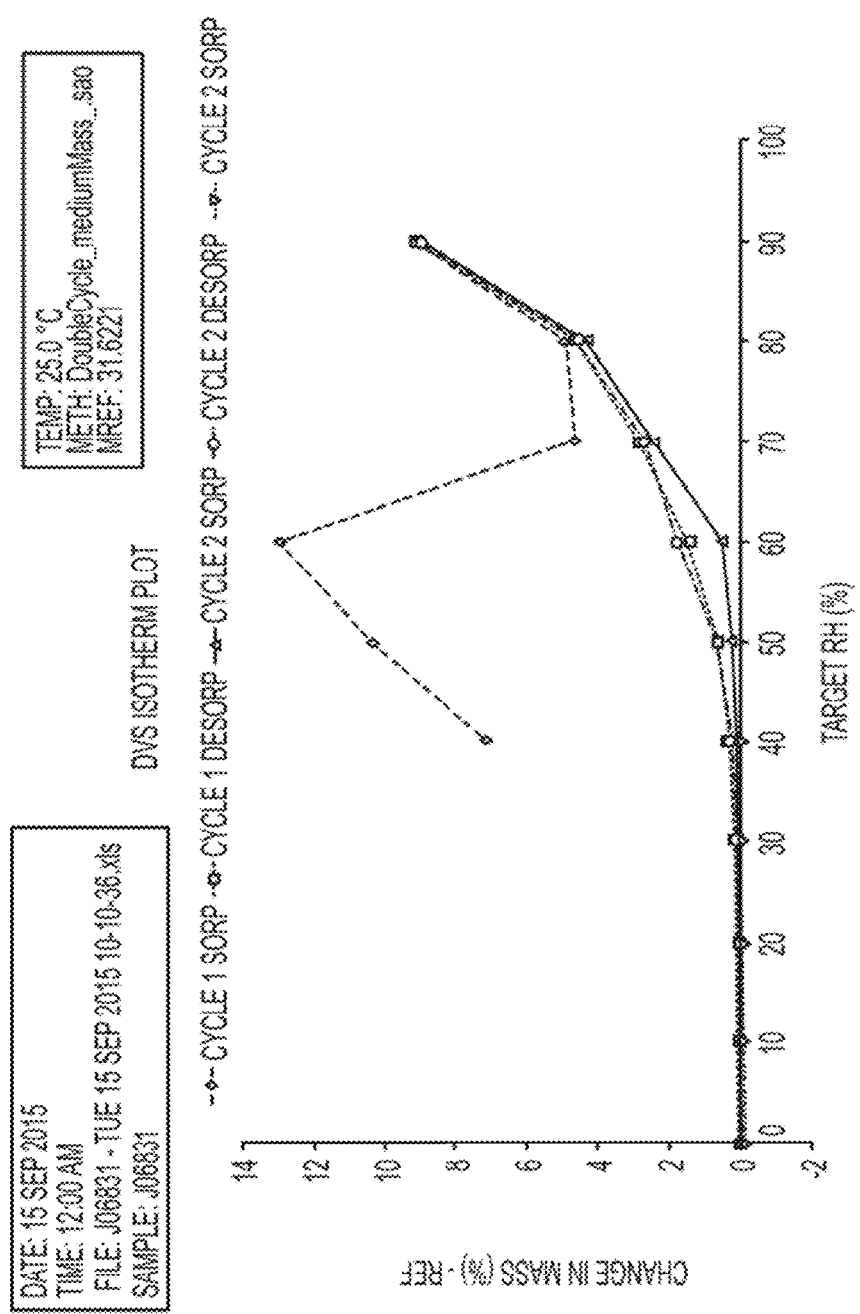
FIG. 6 shows a dynamic vapor sorption isotherm for amorphous NMN.

In certain embodiments, an anhydrous crystalline compound of formula (I) has an XRD pattern substantially as shown in FIG. 1, labeled Form 1.

In certain embodiments, a crystalline compound of formula (I) is not solvated (e.g., the crystal lattice does not comprise molecules of a solvent). In certain alternative embodiments, a crystalline compound of formula (I) is solvated.

In certain embodiments, a crystalline DMSO solvate of the compound of formula (I) has 2θ values 8.29; 17.39; 19.54; 22.78; and 22.98. In further embodiments, the crystalline DMSO solvate has 2θ values 8.29; 17.39; 19.54; 19.74; 20.98; 21.58; 22.03; 22.78; 22.98; and 25.53. In yet further embodiments, the crystalline DMSO solvate has 2θ values 8.29; 16.10; 17.39; 19.24; 19.54; 19.74; 20.33; 20.78; 20.98; 21.18; 21.58; 22.03; 22.78; 22.98; 25.53; 28.48; and 29.48. In further embodiments, the crystalline DMSO solvate has 2θ values 8.29; 13.12; 15.79; 16.10; 16.69; 17.39; 19.03; 19.24; 19.54; 19.74; 20.33; 20.78; 20.98; 21.18; 21.58; 22.03; 22.78; 22.98; 23.95; 24.14; 24.48; 24.64; 25.14; 25.53; 25.87; 26.89; 27.18; 27.67; 28.02; 28.13; 28.48; 28.98; 29.34; 29.48; and 29.92.

The certain embodiments, a crystalline DMSO solvate of the compound of formula (I) has an XRD pattern substantially as shown in FIG. 1, labeled Form 2.

In certain embodiments, the crystalline DMSO solvate of the compound of formula (I) contains about 1.0, about 1.1, or about 1.2 molecules of DMSO to one molecule of NMN.

In certain embodiments, the invention relates to a pharmaceutical composition comprising a crystalline compound of formula (I) and one or more pharmaceutically acceptable excipients. In certain embodiments, the pharmaceutical composition is selected from tablets, capsules, and suspensions.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

Methods of Making the Crystalline Forms of NMN

In certain embodiments, the invention relates to a method for the preparation of a crystalline compound having the structure of formula (I), comprising a) providing a mixture of a compound of formula (I) in a solvent; and b) crystallizing the compound of formula (I) from the mixture comprising the compound of formula (I).

In certain embodiments, the mixture comprising the compound of formula (I) is a solution. In certain embodiments, the mixture is a slurry or a suspension.

In certain embodiments, the crystalline compound made by the methods of the invention is anhydrous.

In certain embodiments, the crystalline compound made by the methods of the invention is a solvate, e.g., a DMSO solvate.

In certain embodiments, the mixture comprising the compound of formula (I) is a solution, and the step of crystallizing the compound from the mixture comprises bringing the solution to supersaturation to cause the compound of formula (I) to precipitate out of solution.

In certain embodiments, bringing the mixture comprising the compound of formula (I) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the compound of formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the crystals, e.g., by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, the solvent comprises acetonitrile, N,N-dimethylacetamide (DMA), dimethylformamide (DMF), dimethylsulfoxide (DMSO), ethanol, ethyl acetate, heptanes, hexanes, isopropyl acetate, methanol, methylethyl ketone, N-methyl-2-pyrrolidone (NMP), tetrahydrofuran, toluene, 2-propanol, 1-butanol, water, or any combination thereof. In certain preferred embodiments, for example to achieve Form 1, the solvent is methanol or water. In other preferred embodiments, for example to achieve Form 2, the solvent is dimethylsulfoxide.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is methanol.

In certain embodiments, washing the crystals comprises washing the crystalline compound of formula (I) with a solvent or a mixture of one or more solvents, which are described above. In certain embodiments, the solvent or mixture of solvents is cooled prior to washing.

In certain embodiments, the methods of making the crystalline forms of NMN are used to remove one or more impurities from NMN. In certain embodiments, the crystallization methods described herein are used for purifying NMN, e.g., as a final purification step in the manufacture of the compound.

Uses of Crystal Forms of NMN

NMN is produced from nicotinamide in the NAD biosynthesis pathway, a reaction that is catalyzed by Nampt. NMN is further converted to NAD in the NAD biosynthesis pathway, a reaction that is catalyzed by Nmnat. "Nicotinamide Adenine Dinucleotide" (NAD), which corresponds to the following structure,

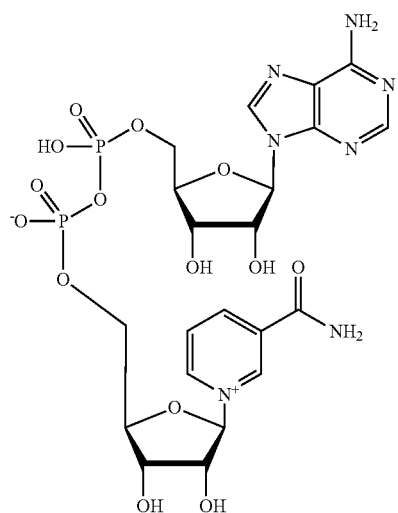

is produced from the conversion of nicotinamide to NMN, which is catalyzed by Nampt, and the subsequent conversion of NMN to NAD, which is catalyzed by Nmnat. In mammals, the functional homolog of yeast PNC1 is NAMPT, which also catalyzes the first step in NAD salvage. NAMPT catalyzes the formation of nicotinamide mononucleotide (NMN) from NAM, which is then converted to NAD by NMNAT1, NMNAT2, and NMNAT3. Nicotinamide riboside, a precursor to NAD, enters the salvage pathway after being converted to NMN by nicotinamide riboside kinase (NRK) enzymes.

Thus, diseases, disorders and conditions that are affected by increasing NAD levels are likewise affected by the amount of NMN precursor available for NAD biosynthesis, and thus can be treated by administering the NMN compounds and compositions disclosed herein.

In certain embodiments, NMN works through the nicotinamide mononucleotide adenylyltransferase (Nmnat1) pathway or other pathways of NAD+ biosynthesis which have nutritional and/or therapeutic value in improving plasma lipid profiles, prevention of stroke, and/or prolonging life and well-being. Other embodiments relate to a method for preventing or treating a disease or condition associated with the nicotinamide mononucleotide adenylyltransferase (Nmnat1) pathway or other pathways of NAD+ biosynthesis by administering a composition comprising NMN. Diseases or conditions which typically have altered levels of NAD+ or its precursors which can be prevented or treated by supplementing a diet or therapeutic treatment regime with NMN and/or NAD+ include, but are not limited to, lipid disorders, (e.g., dyslipidemia, hypercholesterolaemia or hyperlipidemia), stroke, type I and II diabetes, cardiovascular disease, and other physical problems associated with obesity.

Neurodegenerative Diseases

Axon degeneration occurs frequently in neurodegenerative diseases and peripheral neuropathies. The degeneration of transected axons is delayed in Wallerian degeneration slow (Wlds) mice with the overexpression of a fusion protein with the nicotinamide adenine dinucleotide (NAD+) synthetic enzyme, nicotinamide mononucleotide adenylyltransferase (Nmnat1). Both Wld(s) and Nmnat1 themselves are functional in preventing axon degeneration in neuronal cultures.

NAD+ levels decrease in injured, diseased, or degenerating neural cells and preventing this NAD+ decline efficiently protects neural cells from cell death. See, Araki & Milbrandt "Increased nuclear NAD+ biosynthesis and SIRT1 activation prevent axonal degeneration" Science. 2004 Aug. 13; 305(5686):1010-3 and Wang et al., "A local mechanism mediates NAD-dependent protection of axon degeneration" J Cell Biol. 170(3):349-55 (2005) hereby incorporated by reference in their entirety. As NMN is capable of increasing intracellular levels of NAD+, NMN is useful as a therapeutic or nutritional supplement in managing injuries, diseases, and disorders affecting the central nervous system and the peripheral nervous system, including, but not limited to, trauma or injury to neural cells, diseases or conditions that harm neural cells, and neurodegenerative diseases or syndromes. The correlation of increased NAD+ synthesis with beneficial outcomes in neural injuries and diseases or conditions has been discussed in, e.g., Stein et al., "Expression of Nampt in Hippocampal and Cortical Excitatory Neurons Is Critical for Cognitive Function" The Journal of Neuroscience 2014 34(17):5800-5815; and Stein et al., "Specific ablation of Nampt in adult neural stem cells recapitulates their functional defects during aging" EMBO J. 2014 33:1321-1340.

Some neurodegenerative diseases, neurodegenerative syndromes, diseases and conditions that harm neural cells, or otherwise cause injury to neural cells are described below.

Essential tremor (ET) is the most common movement disorder. It is a syndrome characterized by a slowly progressive postural and/or kinetic tremor, usually affecting both upper extremities.

Parkinson's disease (PD) is a progressive neurodegenerative disorder associated with a loss of dopaminergic nigrostriatal neurons.

Alzheimer's disease (AD) is the most common form of dementia. It is a progressive degenerative disease of the brain, strongly associated with advanced age. Over time, people with the disease lose their ability to think and reason clearly, judge situations, solve problems, concentrate, remember useful information, take care of themselves, and even speak. A number of neurodegenerative diseases such as Alzheimer's disease execute their biological impact in the brain. It is preferred that nicotinamide mononucleotide based compounds disclosed herein are capable of passing the blood-brain-barrier (BBB).

Huntington's disease (HD) is an incurable, adult-onset, autosomal dominant inherited disorder associated with cell loss within a specific subset of neurons in the basal ganglia and cortex.

Ataxia is defined as an inability to maintain normal posture and smoothness of movement. Neurologic symptoms and signs such as seizures and movement disorders (e.g., dystonia, chorea) may accompany ataxia.

Catatonia is a state of apparent unresponsiveness to external stimuli in a person who is apparently awake.

Epilepsy is defined as a chronic condition characterized by spontaneous, recurrent seizures; seizure is defined as a clinical event associated with a transient, hypersynchronous neuronal discharge.

Neuroleptic malignant syndrome (NMS) refers to the combination of hyperthermia, rigidity, and autonomic dysregulation that can occur as a serious complication of the use of antipsychotic drugs.

Chorea is an involuntary abnormal movement, characterized by abrupt, brief, nonrhythmic, nonrepetitive movement of any limb, often associated with nonpatterned facial grimaces. Chorea gravidarum (CG) is the term given to chorea occurring during pregnancy.

Cortical basal ganglionic degeneration (CBGD) clinical characteristics include progressive dementia, parkinsonism, and limb apraxia. Dysfunction of the central or peripheral nervous system pathways may cause autonomic dysfunction.

Dystonia is a syndrome of sustained muscle contractions, usually producing twisting and repetitive movements or abnormal postures. Writer's cramp is a form of task-specific focal dystonia.

Mental retardation (MR) is a condition in which intellectual capacity is limited significantly. Developmental disability describes a condition that limits an individual's ability to perform activities and roles as expected in a certain social environment. Frequently, MR and developmental disabilities are present simultaneously as a consequence of brain damage.

Neuroacanthocytosis is a progressive neurologic disease characterized by movement disorders, personality changes, cognitive deterioration, axonal neuropathy, and seizures. Most patients have acanthocytosis on peripheral blood smear at some point during the course of the disease.

Pelizaeus-Merzbacher disease (PMD) and X-linked spastic paraplegia type 2 (SPG2) are at opposite ends of a clinical spectrum of X-linked diseases caused by mutations of the same gene, the proteolipid protein 1 (PLP1) gene, and resulting in defective central nervous system (CNS) myelination. Clinical signs usually include some combination of nystagmus, stridor, spastic quadriparesis, hypotonia, cognitive impairment, ataxia, tremor, and diffuse leukoencephalopathy on MRI scans.

Progressive supranuclear palsy (PSP), also known as Steele-Richardson-Olszewski syndrome, is a neurodegenerative disease that affects cognition, eye movements, and posture.

Striatonigral degeneration (SND) is a neurodegenerative disease that represents a manifestation of multiple system atrophy (MSA). The other manifestations are Shy-Drager syndrome (e.g., autonomic failure predominates) and sporadic olivopontocerebellar degeneration (sOPCA, cerebellum predominates).

Ischemic stroke occurs due to a loss of blood supply to part of the brain, initiating the ischemic cascade. Brain tissue ceases to function if deprived of oxygen for more than 60 to 90 seconds and after a few hours will suffer irreversible injury possibly leading to death of the tissue, i.e., infarction. Atherosclerosis may disrupt the blood supply by narrowing the lumen of blood vessels leading to a reduction of blood flow, by causing the formation of blood clots within the vessel, or by releasing showers of small emboli through the disintegration of atherosclerotic plaques. Embolic infarction occurs when emboli formed elsewhere in the circulatory system, typically in the heart as a consequence of atria fibriliation, or in the carotid arteries. These break off, enter the cerebral circulation, then lodge in and occlude brain blood vessels.

Due to collateral circulation within the region of brain tissue affected by ischemia, there is a spectrum of severity. Thus, part of the tissue may immediately die while other parts may only be injured and could potentially recover. The ischemia area where tissue might recover is referred to as the ischemic penumbra.

As oxygen or glucose becomes depleted in ischemic brain tissue, the production of high energy phosphate compounds such as adenine triphosphate (ATP) fails, leading to failure of energy dependent processes necessary for tissue cell survival. This sets off a series of interrelated events that result in cellular injury and death. These include the failure of mitochondria, which can lead further toward energy depletion and may trigger cell death due to apoptosis. Other processes include the loss of membrane ion pump function leading to electrolyte imbalances in brain cells. There is also the release of excitatory neurotransmitters, which have toxic effects in excessive concentrations.

Spinal cord injury, or myelopathy, is a disturbance of the spinal cord that results in loss of sensation and mobility. The two common types of spinal cord injury are: trauma: automobile accidents, falls, gunshots, diving accidents, etc. and disease: polio, spina bifida, tumors, Friedreich's ataxia, etc. It is important to note that the spinal cord does not have to be completely severed for there to be a loss of function. In fact, the spinal cord remains intact in most cases of spinal cord injury.

Traumatic brain injury (TBI), also called intracranial injury, or simply head injury, occurs when a sudden trauma causes brain damage. TBI can result from a closed head injury or a penetrating head injury and is one of two subsets of acquired brain injury (ABI). The other subset is non-traumatic brain injury (e.g., stroke, meningitis, anoxia). Parts of the brain that can be damaged include the cerebral hemispheres, cerebellum, and brain stem. Symptoms of a TBI can be mild, moderate, or severe, depending on the extent of the damage to the brain. Outcome can be anything from complete recovery to permanent disability or death. A coma can also affect a child's brain. The damage from TBI can be focal, confined to one area of the brain, or diffuse, involving more than one area of the brain. Diffuse trauma to the brain is frequently associated with concussion (a shaking of the brain in response to sudden motion of the head), diffuse axonal injury, or coma. Localized injuries may be associated with neurobehavioral manifestations, hemiparesis or other focal neurologic deficits.

Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients (particularly those who have suffered a cardiac arrest), or in people who suffer significant blood loss from other injuries that then causes a decrease in blood flow to the brain due to circulatory (hypovolemic) shock.

Regulating Blood Glucose Concentration

Provided herein is a process for regulating the concentration of blood glucose in a mammal. As utilized herein, regulating the concentration of blood glucose refers to any increase, decrease, and/or maintenance in or of the concentration of blood glucose as compared to a previously determined level.

NMN may be administered to a mammal in need of such treatment. For example, the mammal may require an increase in blood glucose concentration. Alternatively, the mammal may require a decrease in blood glucose concentration. Or, the mammal may require maintenance of blood glucose concentration above, at, or below a particular level or within a particular range (e.g., through a series of increases and/or decreases, or through no increases or decreases). The blood glucose concentration-regulating NMN may also be administered to a mammal as a prophylactic measure; that is, the mammal is in need of treatment to prevent or delay the occurrence or onset of a medical condition such as, for example, type 1 or type 2 diabetes.

The ability to regulate the concentration of blood glucose in a mammal according to the processes described herein (e.g., by administering to a mammal a blood glucose regulating amount of a compound of the present invention may be advantageous in the treatment and/or prevention of a variety of complications, diseases, and/or illnesses. The role of increased NAD+ levels on metabolic diseases and conditions has been described in, for example, Yoshino et al., "Nicotinamide mononucleotide, a key NAD+ intermediate, treats the pathophysiology of diet- and age-induced diabetes" Cell Metab. 2011 14:528-536; and Garten, et al., "Nampt: Linking NAD biology, metabolism, and cancer" Trends Endocrinol Metab. 2009 20(3):130-138. In general, the present invention may be utilized to treat a variety of acute, intermediate stage, and chronic conditions that may be affected by systemic NAD biosynthesis either directly or indirectly.

For example, the regulation of blood glucose concentration may be effective in the treatment and/or prophylaxis of such medical conditions as brain ischemia-induced hypoglycemia, hypoglycemic brain injury caused by, e.g., congenital hyperinsulinism in children, and/or other conditions that severely reduce blood glucose levels. Alternatively, the regulation of blood glucose concentration may be effective in counteracting the effects of the injection of an excessive amount of insulin, or an insufficient dietary or vitamin intake (e.g., deficiencies in vitamin B3 (niacin, which is derived from nicotinic acid and nicotinamide) can result in pellagra, the classic niacin deficiency disease, characterized by bilateral dermatitis, diarrhea, and dementia).

Further, regulation of blood glucose concentration may be effective in the treatment and/or prophylaxis of hypoglycemia, hyperglycemia, impaired glucose tolerance, impaired fasting glucose, and type 1 and type 2 diabetes.

The regulation of blood glucose concentration according to the methods described herein may also be advantageous in counteracting the effects of blood glucose concentration-decreasing drugs such as acetaminophen, alcohol, anabolic steroids, clofibrate, disopyramide, gemfibrozil, monoamine oxidase inhibitors (MAOIs), pentamidine, or sulfonylurea medications (such as glipizide, glyburide, and glimepiride).

Other conditions having a plausible connection to NAD biosynthesis, such as dementia, may also be beneficially treated and/or prevented by blood glucose regulation. See, e.g., Guest, et al., "Changes in Oxidative Damage, Inflammation and [NAD(H)] with Age in Cerebrospinal Fluid" PLOS One. January 2014 9(1):e85335.

The increase, decrease, and/or maintenance of blood glucose concentration can be quantified, for example, by percentage above, below, or in between one or more previously determined levels, or can be quantified by a particular blood glucose concentration or a range thereof.

For example, the blood glucose concentration may be increased to at least about 5% above a previously determined level; to at least about 10% above a previously determined level; to at least about 25% above a previously determined level; to at least about 50% above a previously determined level; to at least about 75% above a previously determined level; to at least about 100% above a previously determined level; to at least about 150% above a previously determined level; or to at least about 200% above a previously determined level. By way of another example, the blood glucose concentration may be decreased to at least about 5% below a previously determined level; to at least about 10% below a previously determined level; to at least about 25% below a previously determined level; to at least about 50% below a previously determined level; to at least about 75% below a previously determined level; to at least about 100% below a previously determined level; to at least about 150% below a previously determined level; or to at least about 200% below a previously determined level. By way of yet another example, the blood glucose concentration may be maintained (e.g., by a series of increases and/or decreases, or by no increases and/or decreases) at a concentration that is no more than about 50% greater or about 50% less than a previously determined level; e.g., no more than about 40% greater or about 40% less; no more than about 30% greater or about 30% less; no more than about 20% greater or about 20% less; no more than about 10% greater or about 10% less; or no more than about 5% greater or about 5% less.

Alternatively, the blood glucose concentration may be maintained (e.g., by a series of increases and/or decreases, or by no increases and/or decreases) at, above, or below a particular blood glucose concentration or within a desired range of blood glucose concentrations. For example, the blood glucose concentration may be maintained at a concentration of greater than about 60 mg/dL; greater than about 70 mg/dL; greater than about 100 mg/dL; greater than about 110 mg/dL; or greater than about 125 mg/dL. Alternatively, the blood glucose concentration may be maintained at a concentration of less than about 200 mg/dL; less than about 175 mg/dL; less than about 150 mg/dL; less than about 125 mg/dL; less than about 110 mg/dL; or less than about 100 mg/dL. By way of another example, the blood glucose concentration may be maintained at a concentration of from about 60 mg/dL to about 140 mg/dL; from about 90 mg/dL to about 130 mg/dL; from about 100 mg/dL to about 125 mg/dL; or from about 110 mg/dL to about 125 mg/dL.

Drug Toxicity

In some embodiments, the invention relates to the use of NMN to prevent adverse effects and protect cells from toxicity. Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (e.g., superoxide, peroxides, hydroxyl radicals). Repair systems in the cell excise and repair damage caused by toxins.

Enzymes that use NAD+ play a part in the DNA repair process. For example, DNA repair syndromes include, but are not limited to, Cockayne syndrome. Specifically, the poly(ADP-ribose) polymerases (PARPs), particularly PARP-1, are activated by DNA strand breaks and affect DNA repair. The PARPs consume NAD+ as an adenosine diphosphate ribose (ADPR) donor and synthesize poly (ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. See, e.g., Fang, et al., Defective Mitophagy in XPA via PARP-1 Hyperactivation and NAD+/SIRT1 Reduction. Cell 2014 157:882-896. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of NAD+ metabolism in genotoxicity can be partially effective in improving cell survival but that other proteins that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is an important aspect of cell stress response pathways. For example, upregulation of NAD+ metabolism, via nicotinamide/nicotinic acid mononucleotide (NMNAT) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

Aging/Stress

In certain embodiments, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with NMN and/or NAD+. Recent studies have demonstrated the role NAD+ plays in the aging process and in age-related diseases and conditions. See, e.g., Imai, et al., "NAD+ and sirtuins in aging and disease" Trends in Cell Biol. 2014 24(8):464-471; and Gomes, et al. "Declining NAD+ Induces a Pseudohypoxic State Disrupting Nuclear-Mitochondrial Communication during Aging" Cell 2013 155:1624-1638.

The methods described herein may be used to increase the amount of time that cells, particularly primary cells (e.g., cells obtained from an organism, e.g., a human), may be kept alive in an ex vivo cell culture. Embryonic stem(ES) cells and pluripotent cells, and cells differentiated therefrom, may also be treated with a nicotinamide mononucleotide based or derivative compound to keep the cells, or progeny thereof, in culture for longer periods of time. Such cells can also be used for transplantation into a subject, e.g., after ex vivo modification.

In certain embodiments, cells that are intended to be preserved for long periods of time may be treated with NMN and/or NAD+. The cells may be in suspension (e.g., blood cells, serum, biological growth media, etc.) or in tissues or organs in a subject. For example, blood collected from an individual for purposes of transfusion may be treated with NMN and/or NAD+ to preserve the blood cells for longer periods of time. Additionally, blood to be used for forensic purposes may also be preserved using NMN and/or NAD+. Other cells that may be treated to extend their lifespan or protect against apoptosis include cells for consumption, e.g., cells from non-human mammals (such as meat) or plant cells (such as vegetables).

NMN and/or NAD+ may also be applied during developmental and growth phases in mammals, plants, insects or microorganisms, in order to, e.g., alter, retard or accelerate the developmental and/or growth process.

In certain embodiments, NMN and/or NAD+ may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with NMN and/or NAD+ prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with NMN and/or NAD+ or may have a subset of cells/tissue treated locally with NMN and/or NAD+. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In certain embodiments, cells may be treated with an amount of NMN that increases the level of NAD+ in vivo, e.g., to increase their lifespan or prevent apoptosis. For example, skin can be protected from aging (e.g., developing wrinkles, loss of elasticity, etc.) by treating skin or epithelial cells with an amount of NMN that increases the level of intracellular NAD+. In exemplary embodiments, skin is contacted with a pharmaceutical or cosmetic composition comprising an amount of NMN that increases the level of intracellular NAD+. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In other embodiments, an amount of NMN that increases the level of intracellular NAD+ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising an amount of NMN that increases the level of intracellular NAD+ may also be used as preventive, e.g., chemopreventive, compositions. When used in a chemopreventive method, susceptible skin is treated prior to any visible condition in a particular individual.

In certain embodiments, an amount of NMN that increases the level of intracellular NAD+ may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In certain embodiments, an amount of NMN that increases the level of intracellular NAD+ may be administered to a subject in order to generally increase the lifespan of its cells and to protect its cells against stress and/or against apoptosis. Treating a subject with NMN may be similar to subjecting the subject to hormesis, i.e., mild stress that is beneficial to organisms and may extend their lifespan.

An amount of NMN that increases the level of intracellular NAD+ can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

An amount of NMN that increases the level of intracellular NAD+ can also be administered to a subject suffering from an acute disease, e.g., damage to an organ or tissue, e.g., a subject suffering from stroke or myocardial infarction or a subject suffering from a spinal cord injury. An amount of NMN that increases the level of intracellular NAD+ may also be used to repair an alcoholic's liver.

Cardiovascular Disease

In certain embodiments, the invention provides methods for treating and/or preventing a cardiovascular disease by administering to a subject in need thereof an amount of NMN that increases the level of intracellular NAD+. The benefits of NAD+ in treating cardivasular diseases has been described in several studies, such as Borradaile, et al., "NAD+, Sirtuins, and Cardiovascular Disease" Current Pharmaceutical Design 2016 15(1):110-117.

Cardiovascular diseases that can be treated or prevented by an amount of NMN that increases the level of intracellular NAD+ include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems.

Yet other disorders that may be treated with an amount of NMN that increases the level of intracellular NAD+ include restenosis, e.g., following coronary intervention, and disorders relating to an abnormal level of high density and low density cholesterol. Another disease that can benefit from NAD+ treatment is nonalcoholic steatohepatitis (NASH) which a fatty liver disease.

Circadian Rhythm

The circadian clock is encoded by a transcription-translation feedback loop that synchronizes behavior and metabolism with the light-dark cycle. It has been unexpectedly discovered that both the rate-limiting enzyme in mammalian NAD+ biosynthesis, nicotinamide phosphoribosyltransferase (NAMPT), and levels of NAD+, display circadian oscillations which are regulated by the core clock machinery in mice. Inhibition of NAMPT promotes oscillation of the clock gene Per2 by releasing CLOCK:BMAL1 from suppression by SIRT1. In turn, the circadian transcription factor CLOCK binds to and up-regulates Nampt, thus completing a feedback loop involving NAMPT/NAD$^+$ and SIRT1/CLOCK:BMAL1. See, e.g., Ramsey et al., "Circadian clock feedback cycle through NAMPT-mediated NAD+ biosynthesis" Science 2009 324:651-654.

Thus, the periodic variation in NAMPT-mediated NAD+ biosynthesis suggests that it impacts physiologic cycles and possibly the sleep-wake and fasting-feeding cycle. Without being bound by a single theory, it is believed that NAD+ serves as a critical "metabolic oscillator" for the rhythmic regulation of response to environmental cues through control of SIRT1 activity. Compounds disclosed herein may be used to affect a circadian feedback loop through NAMPT-mediated NAD+ biosynthesis and/or a pathway underlying the temporal coupling of metabolic, physiologic, and circadian cycles in mammals.

The recognition of a regulatory pathway involving NAMPT/NAD$^+$-SIRT1/CLOCK:BMAL1 has broad implications for understanding how physiologic and behavioral cycles are coordinated with the environmental light-dark cycle. For instance, during sleep, when animals are normally quiescent and fasting, the levels of NAMPT steadily increase, peaking at the beginning of the wakefulness period and coinciding with feeding. As a result of the increase in NAMPT, NAD$^+$ rises to stimulate SIRT1, which orchestrates an appropriate metabolic response in liver involving a switch from catabolic to anabolic pathways.

In certain embodiments, the present invention provides methods for regulation of the core clock machinery (sometimes also referred to as the circadian clock) of a mammal, thereby affecting behaviors, activities, and/or biological functions that occur in or are affected by a diurnal or circadian cycle and that are regulated, at least in part, by the circadian clock. Generally, the methods involve the administration of a therapeutic or prophylactic amount of a circadian clock-regulating compound to a patient or mammal in need of regulation of the circadian clock.

The methods of treatment disclosed herein are generally directed to methods of regulating the circadian clock, thereby regulating or affecting biological functions that are regulated by (sometimes also said to be affected by, affiliated with, or mediated by) the activity of the circadian clock. Typically, these biological functions display a pattern of activity and inactivity that is generally repeated approximately every 24 hours, oscillating between "active" and "inactive" states during the 24 hour period.

Thus, the present invention provides methods of regulating the activity of the circadian clock by administering to a mammal in need thereof a circadian-clock regulating compound. Generally, the regulation of the activity of the circadian clock is the result of the regulation of CLOCK: BMAL1, which is achieved according to the present methods by regulating the activity of SIRT1. The activity of SIRT1 is generally regulated according to the present methods by administration of a circadian clock-regulating compound, and in certain embodiments, by administration of an amount of NMN that affects the NAD+ pathway. The regulation of the circadian clock thereby permits regulation of activities mediated by the circadian clock.

According to the present invention, the activity of the circadian clock may be increased, decreased, or maintained by the administration of a circadian clock-regulating compound. Accordingly, biological functions (sometimes also referred to as biological activities) that are regulated by the activity of the circadian clock may also be increased, decreased, or maintained. In addition, these biological functions may also be time shifted; that is to say, an activity that typically occurs during a particular period, such as for example, during daytime or daylight hours (sometimes also referred to as the light cycle) or during the night or nighttime hours (sometimes also referred to as the dark cycle) may be shifted such that the activity occurs during the dark or light cycle, respectively, instead.

Any of a number of biological functions that are typically affected by the activity of the circadian clock may be regulated by the methods of the present invention. Thus, the present methods may be used to treat disorders or disease states that are the result of, for example, the irregular, inadequate, or pathological function of the circadian clock. Similarly, the present methods may be used to treat disorders or symptomatology caused by exogenous factors that affect the proper function or activity of the circadian clock or that require a "resetting" of the clock. For example, administration of circadian clock-regulating compound to a patient experiencing a metabolic disorder provides therapeutic benefit not only when the patient's serum NMN or NAD level is increased, but also when an improvement is observed in the patient with respect to other disorders that accompany the metabolic disorder, like weight loss or gain. In some treatment regimens, the circadian clock-regulating compound of the invention may be administered to a patient at risk of developing a disorder as described herein or to a patient reporting one or more of the physiological symptoms of such a disorder, even though a diagnosis of a metabolic disorder may not have been made.

Examples of disorders, disease states, or symptomatology that may be treated according to the methods of the present invention include, but are not limited to, travel to or across one or more time zones, a change in work shifts, night shift work, or a change in the physical status of a mammal caused by, for example, pregnancy or administration of medications of any kind. Accordingly, the methods of the present invention may be used to treat or prevent disorders, symptoms of disorders, or symptoms caused by exogenous factors. Such disorders and symptoms may include, for example, metabolic disorders, such as improper cycling or timing of feeding and fasting cycles, hyperglycemia, hypoglycemia, or diabetes; sleep disorders, such as insomnia, advanced sleep phase syndrome, delayed sleep phase syndrome, inconsistent sleep/wake cycles, or narcolepsy or to improve wakefulness in individuals suffering from excessive sleepiness; and symptoms caused by exogenous factors, such as, travel to or across one or more time zones (jet lag), shifting into or out of daylight savings time, a change in work shifts or night shift work, pregnancy, or medications being taken for unrelated diseases or disorders.

Accordingly, in certain embodiments, the present invention is directed to a method of regulating a biological function in a mammal, the function being affected by the circadian clock. The method comprises administering a therapeutic or prophylactic (sometimes also referred to as a circadian clock-regulating) amount of a circadian clock-regulating compound to the mammal. The biological function can be, for example, any one of the biological functions described herein. In certain embodiments, the invention comprises a method of treating a metabolic disorder in a mammal and comprises administering a therapeutic or prophylactic amount of a circadian clock-regulating compound to the mammal. In other embodiments, the invention comprises a method of treating a disorder in a mammal mediated by the function of the circadian clock and comprises administering a therapeutic or prophylactic amount of a circadian clock-regulating compound to the mammal. According to any one of these embodiments, the circadian clock-regulating compound may be, for example, nicotinamide, nicotinamide mononucleotide (NMN), nicotinamide adenine dinucleotide (NAD); salts and prodrugs thereof; nicotinamide phosphoribosyltransferase (NAMPT); and combinations thereof, as described in greater detail below. In other embodiments, the circadian clock-regulating compound may be an antagonist of any one of the compounds listed above, thereby exacting an effect opposite that of nicotinamide, nicotinamide mononucleotide (NMN), nicotinamide adenine dinucleotide (NAD); salts and prodrugs thereof; nicotinamide phosphoribosyltransferase (NAMPT); and combinations thereof.

In certain embodiments, the present invention is directed to a method of regulating metabolic activity of a mammal comprising administering to the mammal a therapeutic amount of a circadian clock-regulating compound. In certain embodiments, the metabolic activity of the mammal is increased. In other embodiments, the metabolic activity is decreased. In yet other embodiments, the metabolic activity of the mammal is maintained at a desired level, thereby preventing fluctuations in activity/inactivity. In still other embodiments, the metabolic activity is caused to occur in the light cycle (as opposed to its typical occurrence in the dark cycle). In other embodiments, the metabolic activity is caused to occur in the dark cycle (as opposed to its typical occurrence in the light cycle). In certain embodiments, the circadian clock-regulating compound is administered to the mammal in order to increase the anabolic activity of the liver (e.g., increase the activity of the metabolic pathways of the liver or shift or switch liver activity from catabolismo anabolism). In other embodiments, the circadian clock-regulating compound is administered to the mammal in order to increase the catabolic activity of the liver (e.g., decrease the activity of the metabolic process).

Mitochondrial Diseases and Metabolic Effects

In addition to regulating circadian rhythms and protect neural cells from cell death, sirtuins such as SIRT3, SIRT4, and SIRT5 are found in mitochondria. SIRT3 is expressed at high levels in metabolically active tissue. Modulation of SIRT3 has a variety of physiological applications for muscle cells including mimicking calorie restriction or exercise, increasing mitochodrial biogenesis or metabolism, sensitizing a cell to glucose uptake, increasing fatty acid oxidation, and decreasing reactive oxygen species. In addition, SIRT3 is demonstrated herein to be involved in promoting cell survival during genotoxic stress. Thus modulation of SIRT3 levels also has applications in mediating cell survival.

Increasing the protein or activity level of SIRT3 in a muscle cell can mimic the benefits of calorie restriction or exercise. In some embodiments, the invention relates to methods for increasing mitochondrial biogenesis or metabolism or for boosting mitochondrial activity/endurance in a muscle cell by contacting a muscle cell with an agent IS that increases the protein or activity level of SIRT3 in the cell. In some embodiments, the invention relates to methods for sensitizing a muscle cell to glucose uptake by contacting a muscle cell with an agent that increases the protein or activity level of SIRT3 in the cell. Further embodiments of the invention relate to methods for increasing fatty acid oxidation in a muscle cell by contacting a muscle cell with an agent that increases the protein or activity level of SIRT3 in the cell. Some embodiments of the invention relate to methods for decreasing reactive oxygen species (ROS) in a muscle cell by contacting the muscle cell with an agent that increases the protein or activity level of SIRT3 in the cell.

Increasing levels of SIRT3 benefits many diseases and disorders affected by metabolism within mitochondria. Increasing SIRT3 may be useful in any subjects in need of metabolic activation of one or more of their muscles, e.g., smooth muscles or cardiac muscles or muscle cells thereof. A subject may be a subject having cachexia or muscle wasting.

Increasing SIRT3 may also be used to increase or maintain body temperature, e.g., in hypothermic subjects. Alternatively, inhibiting SIRT3 may be used to reduce body temperature, e.g., in subjects having fever or hyperthermia.

Generally, activation of SIRT3 may be used to stimulate the metabolism of any type of muscle, e.g., muscles of the gut or digestive system, or the urinary tract, and thereby may be used to control gut motility, e.g., constipation, and incontinence.

Other embodiments in which it would be useful to increase SIRT3 include repair of muscle, such as after a surgery or an accident, increase of muscle mass; and increase of athletic performance.

Thus the invention provides methods in which beneficial effects are produced by contacting one or more muscle cells with an amount of NMN that increases the protein or activity level of SIRT3 in the cell. These methods effectively facilitate, increase or stimulate one or more of the following: mimic the benefits of calorie restriction or exercise in the muscle cell, increase mitochondrial biogenesis or metabolism, increase mitochondrial activity and/or endurance in the muscle cell, sensitize the muscle cell to glucose uptake, increase fatty acid oxidation in the muscle cell, decrease reactive oxygen species (ROS) in the muscle cell, increase PGC-la and/or ucp3 and/or GLUT4 expression in the muscle cell, and activate AMP activated protein kinase (AMPK) in the muscle cell.

Various types of muscle cells can be contacted in accordance with the invention. In some embodiments, the muscle cell is a skeletal muscle cell. In certain embodiments, the muscle cell is a cell of a slow-twitch muscle, such as a soleus muscle cell. The methods of the invention include, in some embodiments, administering, to a subject in need of such treatment, an amount of NMN that increases the protein or activity level of SIRT3 in cells of the subject.

The cell that is contacted or the subject that is treated in the aforementioned methods preferably is a cell in need of SIRT3 increase in protein or activity level. In certain embodiments, the cell is a diseased cell of a subject.

Also provided are methods for regulating skeletal muscle metabolism or skeletal muscle energy homeostasis in a subject. In such methods, an agent that modulates the protein or activity level of SIRT3 in the subject, i.e., the SIRT3 modulators described herein, is administered to a subject in need thereof.

Also provided are methods for increasing the protein level of SIRT3 in a muscle cell or in muscles of a subject. Such methods include subjecting a cell or a subject to caloric restriction or fasting, or administering to a subject in need thereof an amount of NMN that increases the protein or activity level of SIRT3 in a muscle cell. Diseases, disorders and conditions in which such methods are useful include mitochondrial diseases, metabolic disorders, neurologic disorders, muscular disorders, cardiovascular diseases, and excessive weight or obesity. Specific metabolic disorders, diseases or conditions include insulin resistance, diabetes, diabetes related conditions or disorders, or metabolic syndrome. Other metabolic disorders will be known to the skilled person.

Mitochondrial diseases that can be treated include diseases that show a variety of symptoms caused by dysfunction of mitochondria in cells. The mitochondrial diseases may be classified in various ways by biochemical abnormalities, clinical symptoms or types of DNA abnormalities. Types named as KSS (chronic progressive external ophthalmoplegia), MERRF (myoclonus epilepsy associated with ragged-red fibers; Fukuhara syndrome), MELAS, Leber's disease, Leigh encephalopathia and Pearson's disease are widely known. Among them, MELAS is a type mainly showing stroke-like episodes, occupies 30% or more of the whole and is believed to be the most frequent type in the mitochondrial disease.

In certain embodiments, NMN is useful in treating diseases or disorders associated with DNA repair defects or mitochondrial dysfunction (e.g., resulting from the deregulation of mitochondrial homeostasis). In some embodiments, "mitochondrial dysfunction" or "deregulation of mitochondrial homeostasis" means that one or more mitochondrial component (e.g., ETC component) is depleted, for example by a decrease in mitochondrial gene expression or mitochondrial DNA content, resulting in compromised mitochondrial function (e.g., loss of or decreased oxidative phosphorylation (OXPHOS) capacity). Examples of DNA repair diseases include Cockayne syndrome and TTD.

Retinal Diseases and Disorders

Photoreceptor neuronal cell death and vision can be rescued by NMN administration. In certain embodiments, nicotinamide phosphoribosyl transferase (NAMPT)-mediated NAD biosynthesis can play a role in for rod and/or cone PR neuron survival. In certain embodiments, decreased NAD levels can cause impaired mitochondrial function in PR neurons, alterations in TCA cycle metabolites, and can lead to cell death and blindness.

Deleting NAMPT can lead to photoreceptor death, loss of normal retinal structure and function, and vision loss. In some cases, damage to photoreceptor neurons and their function can be reversed with supplementation of NMN, an NAMPT enzymatic reaction product. Disclosed herein are methods of administering NMN to restore NAD levels in the retina. In some embodiments, NMN supplementation can be an effective therapeutic intervention for many retinal degenerative diseases.

Provided herein are methods of treating, preventing, and reducing risk of diseases associated with photoreceptor dysfunction, including, without limitation, age-related macular degeneration (AMD), inherited and acquired retinal diseases such as, without limitation, retinitis pigmentosa (RP), rod and cone dystrophism, and Leber's congenital amaurosis (LCA) by administration of NMN to a subject. In certain embodiments, NMN administration can be an effective intervention for the prevention and/or treatment of orphan retinal degenerative diseases including but not limited to rod dystrophy, cone dystrophy, retinitis pigmentosa, other inherited retinal degenerations, Leber's congenital amaurosis (LCA) and acquired retinal degenerations such as, but not limited to, age-related macular degeneration, photoreceptor degeneration following retinal detachment.

In some embodiments, these methods can comprise administering to a subject a pharmaceutically effective amount of nicotinamide mononucleotide (NMN). In some embodiments, a pharmaceutically effective amount of nicotinamide mononucleotide (NMN) can be an amount effective for increasing retinal NAD levels.

Disclosed herein are methods of treating macular degeneration in a subject. In some embodiments, the methods include treating aberrant retinal NAD levels in a subject, including aberrantly low retinal NAD levels. These methods comprise administering NMN to a subject. In some embodiments, the methods include treating retinal degeneration in a subject. In some embodiments, the methods include treating photoreceptor damage in a subject. In some embodiments, the methods include treating photoreceptor degeneration in a subject.

In some embodiments, the methods include treating vision loss associated with retinal degeneration in a subject. In some embodiments, the methods include treating aberrant retinal structure in a subject. In some embodiments, the methods include increasing retinal NAD levels in a subject.

In some embodiments, the methods include reducing the risk of developing macular degeneration in a subject. In some embodiments, the methods include reducing risk of developing aberrant retinal NAD levels in a subject. In some embodiments, the methods include reducing the risk of developing retinal degeneration in a subject. In some embodiments, the methods include reducing the risk of developing photoreceptor damage/degeneration in a subject. In some embodiments, the methods include reducing the risk of developing vision loss associated with retinal degeneration in a subject. In some embodiments, the methods include reducing the risk of developing aberrant retinal structure in a subject.

In some embodiments, the methods include treating a retina disease in a subject. In some embodiments, a retinal disease that can be treated by administration of NMN can be retinitis pigmentosa (RP), Leber'scongenital amaurosis (LCA), rod dystrophy, cone dystrophy, rod-cone dystrophy, cone-rod dystrophy, age-related macular degeneration, photoreceptor degeneration following retinal detachments, or a combination thereof.

In certain embodiments, the crystal forms of β-nicotinamide mononucleotide (NMN) (and formulations prepared using such crystal forms) may be used for treating, ameliorating, mitigating, slowing, arresting, preventing or reversing age-associated obesity in a subject. In some embodiments, the invention relates to methods of treating, ameliorating, mitigating, slowing, arresting, preventing or reversing age-associated increases in blood lipid levels in a subject. In some embodiments, the invention relates to methods of treating, ameliorating, mitigating, slowing, arresting, preventing or reversing age-associated loss of insulin sensitivity in a subject. In some embodiments, the invention relates to methods of treating, ameliorating, mitigating, slowing, arresting, preventing or reversing age-associated impairment of memory function in a subject. In some embodiments, the invention relates to methods of treating, ameliorating, mitigating, slowing, arresting, preventing or reversing age-associated decline in eye function in a subject. In some embodiments, the invention relates to methods of treating, ameliorating, mitigating, slowing, arresting, preventing or reversing age-associated retinal degeneration in a subject. In some embodiments, the invention relates to methods of treating, ameliorating, mitigating, slowing, arresting, preventing or reversing dry eye. In some embodiments, the invention relates to methods of treating, ameliorating, mitigating, slowing, arresting, preventing or reversing age-associated dry eye. In some embodiments, the invention relates to methods of treating, ameliorating, mitigating, slowing, arresting, preventing or reversing infertility.

In some embodiments, the invention provides methods of treating age-associated defects in neural stem/progenitor cell (NSPC) functionality in a subject through administration of a crystal form of NMN or a formulation prepared using such a crystal form. In some embodiments, the invention provides methods of reducing age-associated decrease in a NSPC population in a subject through administration of a crystal form of NMN or a formulation prepared using such a crystal form. In some embodiments, the invention provides methods of maintaining at least one NSPC in a subject through administration of a crystal form of NMN or a formulation prepared using such a crystal form. In some embodiments, the invention provides methods of enhancing NAD biosynthesis in a subject through administration of a crystal form of NMN or a formulation prepared using such a crystal form. In some embodiments, the invention provides methods of promoting NSPC proliferation in a subject, in which the methods comprise administration of a crystal form of NMN, or a formulation prepared using such a crystal form, to the subject. The methods of each of these embodiments can comprise, consist essentially of, or consist of administration of a therapeutically effective amount of a crystal form of NMN or a formulation prepared using such a crystal form.

In some embodiments, the invention provides methods of increasing bone density levels in a subject. In some embodiments, the invention provides methods of treating aberrantly low bone density levels in a subject. In some embodiments, the invention provides methods of treating an age-associated bone density decrease in a subject. In some embodiments, the invention provides methods of treating osteoporosis in a subject. In some embodiments, the invention provides methods of preventing an age-associated bone density decrease in a subject. The methods of each of these embodiments can comprise, consist essentially of, or consist of administration of a therapeutically effective amount of a crystal form of NMN or a formulation prepared using such a crystal form.

In certain embodiments, the invention relates to methods of preventing, methods of reducing risk of, and methods of treating various diseases associated with photoreceptor dysfunction, including, without limitation, age-related macular degeneration (AMD), inherited and acquired retinal diseases such as, without limitation, retinitis pigmentosa (RP), rod and cone dystrophism, and Leber's congenital amaurosis (LCA) by administration of NMN. In various embodiments, administration of an NMN crystal form or a formulation prepared using such a crystal form can be an effective intervention for the prevention and/or treatment of orphan retinal degenerative diseases including but not limited to rod dystrophy, cone dystrophy, retinitis pigmentosa, other inherited retinal degenerations, Leber's congenital amaurosis (LCA) and acquired retinal degenerations such as, but not limited to, age-related macular dengeration photoreceptor degeneration following retinal detachment. In various embodiments, a crystal form of NMN or a formulation prepared using such a crystal form can be administered by any administration route known to skilled artisans, such as, without limitation, oral, parenteral, intraocular, intraperitoneal, intravenous or intramuscular routes. In various embodiments, NMN can be administered with or without an excipient.

In some embodiments, NMN treats an age-related disease. In certain embodiments, the age-related disease is Alzheimer's disease, amniotropic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, sarcopenia, sleep disorders, sepsis and/or stroke. In some embodiments, the mitochondrial disease is mitochondrial myopathy, diabetes mellitus and deafness (DAD), Leber's hereditary optic neuropathy (LHON), Leigh syndrome, neuropathy, ataxia, retinitis pigmentosa and petosis (NARP), myoclonic epilepsy with ragged red fibers (MERRF), myoneurogenic gastrointestinal encephalopathy (MNGIE), mitochondrial myopathy, encephalomyopathy, lactic acidosis, stroke-like symptoms (MELAS), Kearns-Sayre syndrome (KSS), chronic progressive external opthalmoplegia (CPEO) and/or mtDNA depletion.

Examples of diseases, disorders, or conditions associated with mitochondrial dysfunction include, but are not limited to, aging, aging-related diseases, mitochondrial diseases (e.g., Alper's disease, Barth syndrome, beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency/COX deficiency, complex V deficiency, chronic progressive external ophthalmoplegia syndrome, CPT I deficiency, CPT II deficiency, Kearns-Sayre syndrome, lactic acidosis, long-chain acyl-CoA dehydrongenase deficiency, Leigh syndrome, Luft disease, glutaric aciduria type II, mitochondrial cytopathy, mitochondrial DNA depletion, mitochondrial encephalopathy, mitochondrial myopathy, and Pearson syndrome), metabolic diseases and disorders (e.g., amino acid deficiency), diseases resulting from mitochondrial and energy deficiency, lethargy, heart disorders, cardiovascular disease, stroke, infarction, pulmonary hypertension, ischemia, cachexia, sarcopenia, neurodegenerative diseases (e.g., Alzheimer's disease, Parkinson's disease, Huntington's disease), dementia, lipodystrophy, liver steatosis, hepatitis, cirrhosis, kidney failure, preeclampsia, male infertility, obesity, diabetes (e.g., diabetes type I), muscle disorders, and muscle wasting.

In some embodiments, NMN is useful for promoting cell viability (in various species), vascular remodeling, wound healing and healing in general (e.g., treating wounds resulting from cuts, scrapes, surgery, bodily insults, trauma, burns, abrasions, sunburns, etc.). In some embodiments, the methods and compositions are useful for promoting iron homeostasis and/or erythropoiesis. In some embodiments, methods and compositions provided herein are useful to promote successful organ and tissue transplantation, or to promote recovery from organ and tissue transplantation. In some embodiments, provided methods and compositions are useful for preserving cells and organs. In some embodiments, methods and compositions provided herein have cosmetic applications, for example for treating conditions associated with mitochondrial dysfunction which relate to the skin or scalp/hair, such as skin aging (e.g., loss in volume and elasticity, discoloration, liver spots (lentigo senislis)), wrinkles, baldness, and loss of hair pigmentation. In some embodiments, agents or compositions described herein are useful for products or methods relating to cosmetics, energy drinks, and/or animal and plant industries (e.g. livestock, pets and agricultural products).

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, NMN may be administered to farm animals to improve their ability to withstand farming conditions longer.

The compound may also be used to increase lifespan, stress resistance, and resistance to apoptosis in plants. In certain embodiments, NMN is applied to plants, e.g., on a periodic basis, or to fungi. In other embodiments, plants are genetically modified to produce NMN. In other embodiments, plants and fruits are treated with NMN prior to picking and shipping to increase resistance to damage during shipping. Plant seeds may also be contacted with NMN, e.g., to preverse them.

NMN may also be used to increase lifespan, stress resistance and resistance to apoptosis in insects. In certain embodiments, NMN would be applied to useful insects, e.g., bees and other insects that are involved in pollination of plants. In preferred embodiments, NMN would be applied to bees involved in the production of honey. Generally, the methods described herein may be applied to any organism, e.g., eukaryote, that may have commercial importance. For example, they can be applied to fish (aquaculture), shrimp, pigs, and birds (e.g., chicken and fowl).

Other uses of NMN include favorably modulating the microbiome or serving as a form of vitamin B3. As the precursor of NAD, NMN could also serve in assays for diseases and conditions affected by NAD biosynthesis, such as use as a standard.

As used herein, a therapeutic that "prevents" a disorder or condition refers to a compound that, in a statistical sample, reduces the occurrence or frequency of the disorder or condition in the treated sample relative to an untreated control sample, or delays the onset or reduces the severity of one or more symptoms of the disorder or condition relative to the untreated control sample. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

Pharmaceutical Compositions

In certain embodiments, the present invention relates to pharmaceutical compositions comprising a crystalline compound of formula (I) and one or more pharmaceutically acceptable excipients, as well as formulations prepared using such a crystalline compound and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient. In certain embodiments, the invention also relates to preparations suitable for nutraceutical, veterinary, and agriculturally-relevant uses.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. Although the dosage will vary depending on the symptoms, age and body weight of the patient, the nature and severity of the disorder to be treated or prevented, the route of administration and the form of the drug, in general, a daily dosage of from 0.01 to 3000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts", J. Pharm. Sci. 66:1-19.).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals.

A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-30% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, dimethylsulfoxide, and the like. Mixtures of such solvates can also be prepared. The source of such solvate can be from the solvent of crystallization, inherent in the solvent of preparation or crystallization, or adventitious to such solvent. In some embodiments, a solvate of a disclosed compound can be a dimethylsulfoxide solvate.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Analytical Methods for Examples 1-5

X-Ray Powder Diffraction

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:
Angular range: 2 to 42° 2θ
Step size: 0.05° 2θ
Collection time: 0.5 s/step
HPLC
Purity analysis was performed on an Agilent HP1100 series system equipped with a diode array detector and using ChemStation software vB.04.03 using the method detailed below in Table 1.

TABLE 1

HPLC Parameters

| Parameter | Value |
| --- | --- |
| Type of method | Reversed phase with gradient elution |
| Sample Preparation | 1 mg/mL in aqueous 20 mM ammonium acetate, pH 5.0 |
| Column | Waters Atlantis C18, 100 Å, 3 µM |
| Column Temperature | 25° C. |
| Injection Volume | 5 µL |
| Detector Wavelength, Bandwidth | 254 nm, 4 nm |
| Flow Rate | 1.0 mL/min |
| Mobile Phase A | 20 mM aqueous ammonium acetate, pH 5.0 |
| Mobile Phase B | methanol |

| | Time (min) | % Mobile Phase A |
| --- | --- | --- |
| Gradient Timetable | 0 | 100 |
| | 5 | 5 |
| | 8 | 5 |
| | 8.1 | 100 |
| | 16.1 | 100 |

Polarised Light Microscopy (PLM)

Samples were studied on a Leica LM/DM polarised light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a λ false-color filter.

Example 1: Synthesis of Form 1 by Crystallisation from Methanol

Amorphous nicotinamide mononucleotide (565 mg) was weighed into a glass vial and methanol (10.0 mL) added. The resulting slurry was stirred at room temperature for 4 h and then a further portion of MeOH (10.0 mL) added. The white solid present was isolated by filtration and then dried under vacuum at room temperature for ca. 16 h to give crystalline beta nicotinamide mononucleotide Form 1, as shown by XRPD analysis. (459 mg, 81% recovery).

Example 2: Synthesis of Form 1 by Crystallisation from Water

Amorphous beta nicotinamide mononucleotide (605 mg) was weighed into a glass vial and deionised water (600 µL) added. After brief vortexing, a clear solution was formed. A portion of this solution (ca. 200 µL) was dispensed into a separate vial and cooled to 5° C. for ca. 16 h. An evolved white solid was isolated by filtration and shown by XRPD analysis to be crystalline beta nicotinamide mononucleotide Form 1 (yield not determined).

Example 3: Synthesis of Form 1 by Vapor Diffusion for SCXRD

Amorphous beta nicotinamide mononucleotide (605 mg) was weighed into a glass vial and deionised water (600 µL) added. After brief vortexing, a clear solution was formed. A portion of this solution (100 µL) was dispensed into a separate vial, which itself was placed into a larger vial containing methanol (500 µL) such that vapor can diffuse freely between both vials. The larger vial was sealed and stored at RT for ca. 16h, after which time a white solid had evolved. This solid was sampled and shown by SCXRD to be crystalline beta nicotinamide mononucleotide Form 1.

Example 4: Synthesis of Form 2

Amorphous beta nicotinamide mononucleotide (568 mg) was weighed into a glass vial and DMSO (10.0 mL) added. The resulting slurry was stirred at room temperature for ca. 20 h. The white solid present was then isolated by filtration, washed with acetone (3×1 mL) and dried under vacuum at room temperature for ca. 16 h to give crystalline beta nicotinamide mononucleotide Form 2 (501 mg, 72% recovery*).

* based on assumption that material is a DMSO monosolvate

Example 5: Three Month Stability and Forced Degradation Study for Amorphous and Crystalline NMN Samples of amorphous NMN and NMN crystalline Form 1 were stored as solids at 25° C./0% Relative Humidity (RH), and 40° C./75% RH for three months. The samples were prepared in duplicate with an offset of 2 weeks. Each replicate was stored in a different container.

Replicate 1 was charged in an open HPLC vial that was placed in a sealed scintillation vial containing a saturated solution of the relevant inorganic salt (Table 2). These samples were analysed by HPLC, 1H NMR, XRPD and Polarized Light Microscopy (PLM) at 4, 8, and 12 week time points.

Replicate 2 was stored in sealed box with a recipient containing a saturated solution of the relevant inorganic salt (Table 2). These samples were analysed by HPLC at 2, 6, 10 and 12 week time points. Samples at 25° C./0% RH were stored in a sealed box containing a desiccant agent ($P_2O_5$).

TABLE 2

| Conditions | Inorganic Salt/Dessicant Agent |
| --- | --- |
| 25° C./0% RH | $P_2O_5$ |
| 25° C./60% RH | $NH_4NO_3$ |
| 25° C./97% RH | $K_2SO_4$ |
| 40° C./75% RH | NaCl |

Amorphous material remained unchanged in terms of solid form and particle morphology after storage for 12 weeks at 25° C., 0% RH. A drop in purity was observed from 98.2% (time 0) to 95.5% (time 12 weeks). The main growing impurity observed by HPLC eluted at RRT 1.73 and corresponded to nicotinamide (2.8% at the 12 weeks' time point). (See Tables 3 and 4.)

TABLE 3

HPLC Purity Profiles of Amorphous NMN and Crystal Form 1 NMN at t = 0

| J07086 (Amorphous) | | RME-1304-063-01 (Crystalline) | |
| --- | --- | --- | --- |
| RRT | Area % | RRT | Area % |
| 0.70 | 0.47 | 0.69 | 0.15 |
| 0.76 | 0.10 | 0.75 | 0.09 |
| 1.00 | 98.56 | 1.00 | 99.52 |
| — | — | 1.31 | 0.06 |
| — | — | 1.46 | 0.01 |

TABLE 3-continued

HPLC Purity Profiles of Amorphous
NMN and Crystal Form 1 NMN at t = 0

| J07086 (Amorphous) | | RME-1304-063-01 (Crystalline) | |
|---|---|---|---|
| RRT | Area % | RRT | Area % |
| — | — | 1.48 | 0.03 |
| — | — | 1.53 | 0.01 |
| 1.76 | 0.87 | 1.74 | 0.12 |

The amorphous material crystallized when stored under 25% or greater relative humidity, giving Form 1 with acicular morphology. Chemical purity was shown to decrease upon storage at all the tested conditions, especially at 40° C./75% RH. The main growing impurity observed was also nicotinamide (RRT=1.73). Purity of the material after 12 weeks at 40° C./75% RH was determined as 67.5% (replicate 2) and the nicotinamide abundance was 20.6%.

Crystalline Form 1 remained unchanged in terms of solid form and particle morphology at all conditions tested. The material remained chemically pure (~99.3%) after 4 weeks of storage at all the tested conditions. A slight drop in purity was observed beyond that time point. Storage at 25° C./0% RH proved to be the most favorable conditions for sample stability as the analysis after 12 weeks showed the sample to be 98.9% pure and 0.38% nicotinamide. The largest change in purity was observed for the samples stored at high temperature (40° C.) or high humidity (75% RH, 97% RH). Purity dropped from 99.5% to 95.8% after 12 weeks at 25°/97% RH and to 90.7% after 12 weeks at 40° C./75% RH. The most abundant impurity at all conditions was nicotinamide (RRT=1.73 min). This impurity increased from 0.12% (time 0) to 3.46% after 12 weeks at both, 40° C./75% RH and 25° C./97% RH.

The HPLC results were consistent among replicates, however, faster degradation was observed with Replicate 1. A potential influence may have been the smaller size of the containers which required less time to equilibrate to the corresponding storage conditions. Tables 4-7 provide results obtained for Replicates 1 and 2.

TABLE 4

Stability and Forced Degradation Study: Results for Amorphous Material Replicate 1

| Sample ID | Conditions | Time Point | Observations | XRPD | Purity (%) | Known Impurity* (%) | PLM |
|---|---|---|---|---|---|---|---|
| J07087_25_0_4w | 25° C., 0% RH | 4 weeks | white solid | Unchanged | 96.9 | 1.81 | Unchanged |
| J07087_25_0_8w | | 8 weeks | white solid | Unchanged | 95.8 | 2.44 | Unchanged |
| J07087_25_0_12w | | 12 weeks | white solid | Unchanged | 95.0 | 2.81 | Unchanged |
| J07087_25_60_4w | 25° C., 60% RH | 4 weeks | brown solid | Form 1 | 96.9 | 2.13 | acicular particles up to ~75-100 μm |
| J07087_25_60_8w | | 8 weeks | brown solid, compacted | Form 1 | 95.2 | 3.46 | — |
| J07087_25_60_12w | | 12 weeks | brown solid, compacted | Form 1 | 95.7 | 3.46 | acicular particles up to ~75-100 μm |
| J07087_25_97_4w | 25° C., 97% RH | 4 weeks | white solid, very wet | Form 1 | 97.1 | 2.44 | acicular particles up to ~75-100 μm |
| J07087_25_97_8w | | 8 weeks | partially deliquesced. yellow liquid | n/a | — | — | — |
| J07087_25_97_12w | | 12 weeks | deliquesced. yellow liquid | n/a | — | — | — |
| J07087_40_75_4w | 40° C., 75% RH | 4 weeks | brown compacted solid | Form 1 | 91.3 | 6.70 | acicular particles up to ~75-100 μm |
| J07087_40_75_8w | | 8 weeks | brown compacted solid | Form 1 | 76.9 | 14.23 | — |
| J07087_40_75_12w | | 12 weeks | black solid, very wet$ | Form 1 | — | — | — |

*nicotinamide (RRT = 1.73 min)
$HPLC analysis not performed as weight could not be stabilised for sample preparation.
$^1$H NMR spectra were consistent with the structure of the materials of all samples.

TABLE 5

Stability and Forced Degradation Study: Results for Crystalline Material Replicate 1

| Sample ID | Conditions | Time Point | Observations | XRPD | Purity (%) | Known Impurity* (%) | PLM |
|---|---|---|---|---|---|---|---|
| RME-1304-63-01_25_0_4w | 25° C., 0% RH | 4 weeks | white solid | Unchanged | 99.4 | 0.25 | acicular particles up to ~75 μm |
| RME-1304-63-01_25_0_8w | | 8 weeks | white solid | Unchanged | 99.2 | 0.33 | acicular particles up to ~75 μm |

TABLE 5-continued

Stability and Forced Degradation Study: Results for Crystalline Material Replicate 1

| Sample ID | Conditions | Time Point | Observations | XRPD | Purity (%) | Known Impurity* (%) | PLM |
|---|---|---|---|---|---|---|---|
| RME-1304-63-01_25_0_12w | | 12 weeks | white solid | Unchanged | 98.9 | 0.38 | acicular particles up to ~75 μm |
| RME-1304-63-01_25_60_4w | 25° C., 60% RH | 4 weeks | light brown solid | Unchanged | 99.3 | 0.34 | acicular particles up to ~75 μm |
| RME-1304-63-01_25_60_8w | | 8 weeks | light brown solid, loose particles | Unchanged | 98.9 | 0.63 | acicular particles up to ~75 μm |
| RME-1304-63-01_25_60_12w | | 12 weeks | light brown solid, loose particles | Unchanged | 98.2 | 0.98 | acicular particles up t o~75 μm |
| RME-1304-63-01_25_97_4w | 25° C., 97% RH | 4 weeks | white solid | Unchanged | 99.3 | 0.49 | acicular particles <75 μm |
| RME-1304-63-01_25_97_8w | | 8 weeks | white solid | Unchanged | 98.3 | 1.38 | acicular particles up to 75-100 μm |
| RME-1304-63-01_25_97_12w | | 12 weeks | white solid, wet | Unchanged | 95.8$ | 3.46 | acicular particles < 75 μm |
| RME-1304-63-01_25_75_4w | 40° C., 75% RH | 4 weeks | white solid | Unchanged | 99.2 | 0.46 | acicular particles up to ~75 μm |
| RME-1304-63-01_25_75_8w | | 8 weeks | white solid with orange spots | Unchanged | 97.7 | 1.38 | acicular particles up to ~75 μm |
| RME-1304-63-01_25_75_12w | | 12 weeks | brown solid, very wet | Unchanged | 90.7 | 3.46 | acicular particles < 75 μm |

*nicotinamide (RRT = 1.73 min)
$Weight could not be stabilised. Approximate value was taken.
$^1$HNMR spectra were consistent with the structure of the materials of all samples.

TABLE 6

Forced Degradation Study Results for Amorphous Material Replicate 2

| Sample ID | Conditions | Time Point | Observations | Purity (%) | Known Impurity * (%) |
|---|---|---|---|---|---|
| J07087_25_60_2w | 25° C., 60% RH | 2 weeks | light yellow solid, very compacted | 97.4 | 2.14 |
| J07087_25_60_6w | | 6 weeks | light brown, compacted | 97.4 | 2.06 |
| J07087_25_60_10w | | 10 weeks | light brown, compacted | 96.0 | 2.92 |
| J07087_R2_25_60_12w | | 12 weeks | light brown, compacted | 96.2 | 2.32 |
| J07087_25_97_2w | 25° C., 97% RH | 2 weeks | white compacted solid | 97.8 | 1.79 |
| J07087_25_97_6w | | 6 weeks | white solid, very wet | 96.5 | 3.01 |
| J07087_25_97_10w | | 10 weeks | white solid, very wet | 94.9 | 4.39 |
| J07087_25_97_12w | | 12 weeks | white solid, very wet | 91.5 | 7.02 |
| J07087_40_75_2w | 40° C., 75% RH | 2 weeks | brown compacted solid | 94.6 | 4.61 |
| J07087_40_75_6w | | 6 weeks | dark brown solid | 88.0 | 8.22 |
| J07087_40_75_10w | | 10 weeks | black solid | 75.9 | 16.18 |
| J07087_R2_40_75_12w | | 12 weeks | black solid, very wet | 67.5$ | 20.60 |

* nicotinamide (RRT = 1.73 min)
$Weight could not be stabilised. Approximate value was taken.

TABLE 7

Forced Degradation Study Results for Amorphous Material Replicate 2

| Sample ID RME-1304-63-01-_ | Conditions | Time Point | Observations | Purity (%) | Known Impurity* (%) |
|---|---|---|---|---|---|
| _25_60_2w | 25° C., | 2 weeks | white solid | 99.6 | 0.19 |
| _25_60_6w | 60% RH | 6 weeks | light brown compacted solid | 99.5 | 0.21 |
| _25_60_10w | | 10 weeks | light brown compacted solid | 99.1 | 0.35 |
| R2_25_60_12w | | 12 weeks | light brown compacted solid | 98.8 | 0.23 |
| _25_97_2w | 25° C., | 2 weeks | white solid | 99.5 | 0.22 |
| _25_97_6w | 97% RH | 6 weeks | white solid, very wet | 99.4 | 0.38 |
| _25_97_10w | | 10 weeks | white solid, wet | 98.6 | 0.77 |
| R2_25_97_12w | | 12 weeks | white solid, wet | 98.4 | 0.55 |
| _40_75_2w | 40° C., | 2 weeks | white solid | 99.5 | 0.22 |
| _40_75_6w | 75% RH | 6 weeks | white solid with orange spots | 99.4 | 0.27 |
| _40_75_10w | | 10 weeks | light brown loose particles | 98.8 | 0.49 |
| R2_40_75_12w | | 12 weeks | light brown loose particles | 97.4 | 0.77 |

*nicotinamide (RRT = 1.73 min)

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of formulating a cosmetic composition for topical application to human skin, said method comprising (a) obtaining an amorphous compound of formula (I):

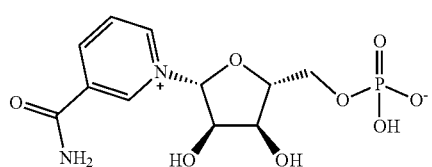

(I)

or a salt thereof,
and (b) adding said compound to one or more components to form the cosmetic composition,
wherein:
the composition is an ointment, paste, cream, lotion, or gel; and
the composition is free of absorption enhancers.

2. The method of claim 1, wherein at least one component for cosmetic topical administration to human skin is a cosmetically acceptable carrier comprising a component selected from the group consisting of a carbohydrate, an antioxidant, and a chelating agent.

3. The method of claim 2, wherein the carrier comprises a carbohydrate.

4. The method of claim 3, wherein the carbohydrate is selected from the group consisting of glucose, sucrose, and dextran.

5. The method of claim 2, wherein the carrier comprises an antioxidant.

6. The method of claim 5, wherein the antioxidant is selected from the group consisting of ascorbic acid, cysteine hydrochloride, sodium bisulfate, sodium metabisulfite, and sodium sulfite.

7. The method of claim 5, wherein the antioxidant is selected from the group consisting of ascorbyl palmitate, butylated hydroxyanisole (BHA), butylated hydroxytoluene (BHT), lecithin, propyl gallate, and alpha-tocopherol.

8. The method of claim 2, wherein the carrier comprises a chelating agent.

9. The method of claim 8, wherein the chelating agent is selected from the group consisting of citric acid, ethylenediamine tetraacetic acid (EDTA), sorbitol, tartaric acid, and phosphoric acid.

10. The method of claim 1, wherein the composition further comprises glycerin.

11. The method of claim 1, wherein the composition further comprises water.

12. The method of claim 1, wherein the composition is pyrogen-free.

13. A method for enhancing well-being, comprising topically administering a composition made by the method of claim 1 to human skin.

14. A method for achieving a cosmetic effect, comprising topically administering a composition made by the method of claim 1 to human skin.

15. The method of claim 14, wherein said cosmetic effect is a cosmetic response to symptoms of aging skin, and further wherein the symptoms of aging skin are selected from wrinkles, loss of elasticity, loss of skin volume, and skin discoloration.

\* \* \* \* \*